(12) United States Patent
Kontrogianni-Konstantopoulos et al.

(10) Patent No.: US 9,739,784 B2
(45) Date of Patent: Aug. 22, 2017

(54) GIANT OBSCURINS AND USES THEREOF IN CANCER PROGNOSIS AND THERAPY

(71) Applicants: Aikaterini Kontrogianni-Konstantopoulos, Ellicott City, MD (US); Konstantinos Konstantopoulos, Ellicott City, MD (US); Marey Shriver, Nottingham, MD (US); Nicole Perry, Baltimore, MD (US)

(72) Inventors: Aikaterini Kontrogianni-Konstantopoulos, Ellicott City, MD (US); Konstantinos Konstantopoulos, Ellicott City, MD (US); Marey Shriver, Nottingham, MD (US); Nicole Perry, Baltimore, MD (US)

(73) Assignees: UNIVERSITY OF MARYLAND, BA, Baltimore, MD (US); JOHNS HOPKINS UNIVERSITY, Baltimore, MD (US)

( * ) Notice: Subject to any disclaimer, the term of this patent is extended or adjusted under 35 U.S.C. 154(b) by 225 days.

(21) Appl. No.: 14/221,755

(22) Filed: Mar. 21, 2014

(65) Prior Publication Data
US 2014/0286932 A1    Sep. 25, 2014

Related U.S. Application Data

(60) Provisional application No. 61/803,873, filed on Mar. 21, 2013.

(51) Int. Cl.
| | | |
|---|---|---|
| *A61K 39/395* | (2006.01) |
| *C12N 5/00* | (2006.01) |
| *C12Q 1/68* | (2006.01) |
| *G01N 33/53* | (2006.01) |
| *G01N 33/574* | (2006.01) |
| *C07K 16/40* | (2006.01) |
| *A61K 45/06* | (2006.01) |
| *C07K 16/18* | (2006.01) |
| *A61K 38/00* | (2006.01) |

(52) U.S. Cl.
CPC ....... *G01N 33/57496* (2013.01); *A61K 45/06* (2013.01); *C07K 16/18* (2013.01); *C07K 16/40* (2013.01); *C12Q 1/6886* (2013.01); *G01N 33/57415* (2013.01); *A61K 38/00* (2013.01); *C12Q 2600/118* (2013.01); *C12Q 2600/158* (2013.01)

(58) Field of Classification Search
None
See application file for complete search history.

(56) References Cited

PUBLICATIONS

Perry et al. Loss of giant obscurins promotes breast epithelial cell survival through apoptotic resistance. Faseb Journal. Published online Mar. 21, 2012; 26(7):2764-2775.*
Shriver et al. Obscurins Invade Breast Cancer Research. Faseb Journal. 2010; 24 (supplement 1).*
Perry et al. Obscurins: Giant proteins with tumor suppressing activities in breast cancer. Faseb Journal. 2010; 24 (supplement 1).*
Ackermann et al., Obscurin Interacts with a Novel Isoform of MyBP-C Slow at the Periphery of the Sarcomeric M-Band and Regulates Thick Filament Assembly. Molecular Biology of the Cell 2009; 20: 2963-2978.
Arjonen et al., Filopodia and adhesion in cancer cell motility. Cell Adh Migr 2011; 5: 421-430.
Balakrishnan et al., Novel Somatic and Germline Mutations in Cancer Candidate Genes in Glioblastoma, Melanoma, and Pancreatic Carcinoma. Cancer Research 2007; 67: 3545-3550.
Balzer et al., Physical confinement alters tumor cell adhesion and migration phenotypes. FASEB J 2012; 26: 4045-4056.
Baum et al., Dynamics of adherens junctions in epithelial establishment, maintenance, and remodelingThe Journal of well Biology 2011; 192: 907-917.
Borisov et al., Developmental Expression and Differential Cellular Localization of Obscurin and Obscurin-Associated Kinase in Cardiac Muscle Cells. Journal of Cellular Biochemistry 2008; 103: 1621-1635.
Brasch et al., Thinking outside the cell: how cadherins drive adhesion. Trends Cell Biol 2012; 22: 299-310.
Bravo-Cordero et al., Directed Cell Invasion and Migration During Metastasis. Curr Opin Cell Biol 2012; 24: 277-281.
Chen et al., Mesothelin Binding to CA125/MUC16 Promotes Pancreatic Cancer Cell Motility and Invasion via MMP-7 Activation. Sci Rep 2013; 3: 1870.
Chiang et al., Molecular Basis of Metastasis. N Engl J Med 2008; 359: 2814-2823.
Dallas et al., Divergent roles of CD44 and carcinoembryonic antigen in colon cancer metastasis. FASEB J 2012; 26: 2648-2656.
Drasin et al., Breast cancer epithelial-to-mesenchymal transition: examining the functional consequences of plasticity. Breast Cancer Res 2011; 13: 226.

(Continued)

*Primary Examiner* — Vanessa L Ford
*Assistant Examiner* — Sandra Dillahunt
(74) *Attorney, Agent, or Firm* — Benjamin Aaron Adler

(57) ABSTRACT

Provided herein are methods and kits for evaluating potential for invasiveness, metastasis, or recurrence of an epithelial cell cancer. In the methods the expression profile of giant obscurins is detected in a tissue sample of tumor cells or suspected tumor cells and assessed for giant obscuring expression level and distribution therein. Decreased levels or altered distribution of giant obscurins in the cells compared to a control non-invasive standard or to a sample taken at a different point in time is indicative of increased potential of at least one of the invasiveness, metastasis, or recurrence of the epithelial cell cancer. The kit comprises a detection reagent suitable for detecting the presence and distribution of giant obscurins or an amount of the gene product(s) encoding giant obscurins in cells of a tissue sample and instructions for using the detection reagent.

4 Claims, 13 Drawing Sheets

(56) References Cited

PUBLICATIONS

Ericson et al., Genetic inactivation of AKT1, AKT2, and PDPK1 in human colorectal cancer cells clarifies their roles in tumor growth regulation. PNAS 2010; 107: 2598-2603.
Ford-Speelman et al., The Rho-Guanine Nucleotide Exchange Factor Domain of Obscurin Activates RhoA Signaling in Skeletal Muscle. Molecular Biology of the Cell 2009; 20: 3905-3917.
Friedl et al., Cancer Invasion and the Microenvironment: Plasticity and Reciprocity. Cell 2011; 147: 992-1009.
E-Cadherin Suppresses Cellular Transformation by Inhibiting Beta-Catenin Signaling in an Adhesion-independent Manner. Gottardi et al., J Cell Biol 2001; 153: 1049-1060.
Hall A. Rho family GTPases. Biochem Soc Trans 2012; 40: 1378-1382.
Hanahan et al., Hallmarks of Cancer: The Next Generation. Cell 2011; 144: 646-674.
BMI1 Cooperates with H-RAS to Induce an Aggressive Breast Cancer Phenotype with Brain Metastases. Hoenerhoff et al., Oncogene 2009; 28: 3022-3032.
Hu et al., The kinase domains of obscurin interact with intercellular adhesion proteins. FASEB J 2013; 27: 2001-2012.
Hung et al., Distinct signaling mechanisms regulate migration in unconfined versus confined spaces. J Cell Biol 2013; 202: 807-824.
Knights et al., Holding Tight: Cell Junctions and Cancer Spread. Trends in Cancer Research 2012; 8: 61-69.
Kontrogianni-Konstantopoulos et al., Obscurin Is a Ligand for Small Ankyrin 1 in Skeletal Muscle. Molecular Biology of the Cell 2003; 14: 1138-1148.
Kontrogianni-Konstantopoulos et al., Muscle Giants: Molecular Scaffolds in Sarcomerogenesis. Physiol Rev 2009; 89: 1217-1267.
Nanda et al.,. Tumor endothelial marker 1 (Tem1) functions in the growth and progression of abdominal tumors. PNAS 2006; 103: 3351-3356.
Perry et al., Loss of giant obscurins promotes breast epithelial cell survival through apoptotic resistance. FASEB J 2012; 26: 2764-2775.
Perry et al., Obscurins: Unassuming Giants Enter the Spotlight. IUBMB life 2013; 65: 479-486.
Phillips et al., The Response of CD24—/low /CD44 + Breast Cancer—Initiating Cells to Radiation. J Natl Cancer Inst 2006; 98: 1777-1785.
Price et al.,Highly accurate two-gene classifier for differentiating gastrointestinal stromal tumors and leiomyosarcomas. PNAS 2007; 104: 3414-3419.
Rago et al., Serial Assessment of Human Tumor Burdens in Mice by the Analysis of Circulating DNA. Cancer Research 2007; 67: 9364-9370.
Samuels et al., Mutant PlK3CA promotes cell growth and invasion of human cancer cells. Cancer Cell 2005; 7: 561-573.
Taube et al., Core epithelial-to-mesenchymal transition interactome gene-expression signature is associated with claudinlow and metaplastic breast cancer subtypes. PNAS USA 2010; 107: 15449-15454.
Tong et al., Chemotaxis of Cell Populations through Confined Spaces at Single-Cell Resolution. PLoS One 2012; 7: e29211.
Valenta et al., The many faces and functions of b-catenin. The EMBO Journal 2012; 31: 2714-2736.
Chhabra et al., The many faces of actin: matching assembly factors with cellular structures. Nat Cell Biol 2007; 9: 1110-1121.
Ciardiello et al., Additive Effects of c-erbB-2, c-Ha-ras, and Transforming—Growth Factor-a Genes on In Vitro Transformation of Human Mammary Epithelial Cells. Molecular carcinogenesis 1992; 6: 43-52.
Foroni et al., Epithelial—mesenchymal transition and breast cancer: Role, molecular mechanisms and clinical impact. Cancer Treat Rev 2012; 38: 689-697.
Fukuzawa et al., Complete human gene structure of obscurin: implications for isoform generation by differential splicing. Journal of Muscle Research and Cell Motility 2005; 26: 427-434.
Holland et al., Wnt signaling in stem and cancer stem cells. Current Opinion in Cell Biology 2013; 25: 254-264.
Kontrogianni-Konstantopoulos et al., Obscurin: a multitasking muscle giant. Journal of Muscle Research and Cell Motility 2005; 26: 419-426.
Kontrogianni-Konstantopoulos et al., Obscurin modulates the assembly and organization of sarcomeres and the sarcoplasmic reticulum. FASEB J 2006; 20: 2102-2111.
Russell et al., Identification, tissue expression and chromosomal localization of human Obscurin-MLCK, a member of the titin and Dbl families of myosin light chain kinases. Gene 2002; 282: 237-246.
Scheel et al., Cancer stem cells and epithelial-mesenchymal transition: Concepts and molecular links. Seminars in cancer Biology 2012; 22: 396-403.
Sjoblom et al.,The Consensus Coding Sequences of Human Breast and Colorectal Cancers. Science 2006; 314: 268-274.
Wang et al., Transforming and oncogenic potential of activated c-Ha-ras in three immortalized human breast epithelial cell lines. Anticancer Research 1997; 17: 4387-4394.

\* cited by examiner

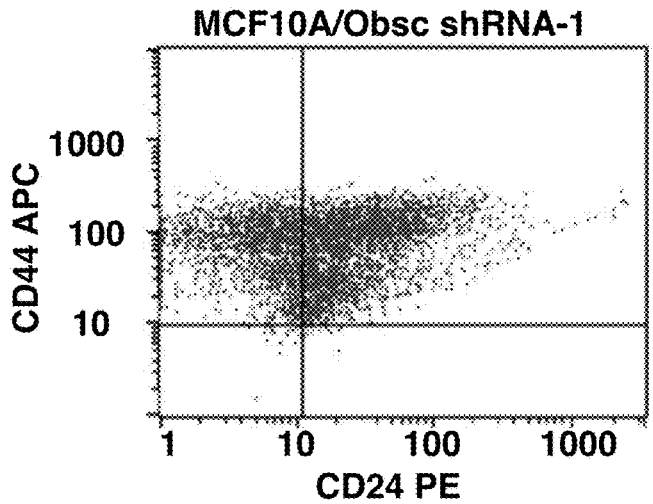
FIG. 2D
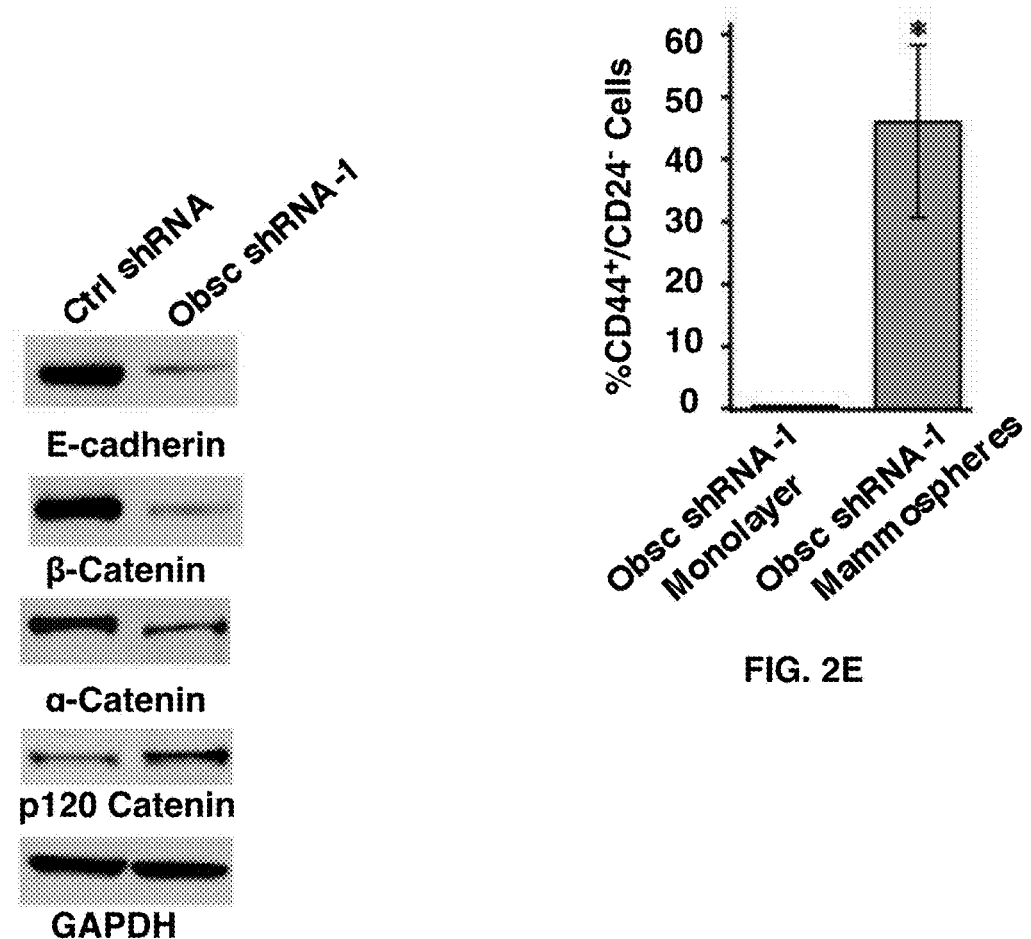
FIG. 2E
FIG. 3A

GIANT OBSCURINS AND USES THEREOF IN CANCER PROGNOSIS AND THERAPY

CROSS-REFERENCE TO RELATED APPLICATION

This non-provisional application claims benefit of priority under 35 U.S.C. §119(e) of provisional U.S. Ser. No. 61/803,873, filed Mar. 21, 2013, the entirety of which is hereby incorporated by reference.

FEDERAL FUNDING LEGEND

This invention was made with government support under Grant Number CA143868 awarded by the National Institutes of Health. The government has certain rights in the invention.

BACKGROUND OF THE INVENTION

Field of the Invention

The present invention is in the field of cancer biology and pharmacotherapy of cancer diseases and conditions. More specifically, the present invention is giant obscurins and uses thereof.

Description of the Related Art

Obscurins comprise a family of giant, multidomain, cytoskeletal proteins originally identified in striated muscles where they play key roles in their structural organization and contractile activity (29, 31, 34). The human OBSCN gene spans 150 kb on chromosome 1q42 and undergoes extensive splicing to give rise to at least 4 isoforms (19, 38). The prototypical form of obscurin, obscurin A, is ~720 kDa and contains multiple signaling and adhesion domains arranged in tandem (31). The $NH_2$-terminus of the molecule contains repetitive immunoglobulin (Ig) and fibronectin-III (Fn-III) domains, while the COOH-terminus includes several signaling domains, including an IQ motif, a src homology 3 (SH3) domain, a Rho-guanine nucleotide exchange factor (Rho-GEF), and a pleckstrin homology (PH) domain, interspersed by non-modular sequences. In addition to obscurin A, the OBSCN gene gives rise to another large isoform, obscurin B or giant (g) MLCK, which has a molecular mass of ~870 kDa (19, 38). Obscurin B contains two serine/threonine kinase domains, which replace the non-modular COOH-terminus of obscurin A (25). The two serine/threonine kinases may also be expressed independently as smaller isoforms, containing one (~55 kDa) or both (~145 kDa) kinase domains (6).

Early sequencing analysis of 13,023 genes in breast and colorectal cancers identified 189 candidate genes that were highly mutated (41). Of the 189 candidate genes, TP53 and OBSCN were the only commonly mutated genes in both tumor types (41). Additional analysis of OBSCN revealed a germline mutation in glioblastoma and novel somatic mutations in melanoma tumors (3). Moreover, whole genome array analysis of gastrointestinal stromal and leiomyosarcoma tumors indicated that the differential expression of OBSCN and PRUNE2 is a reliable two-gene expression classifier that can distinguish the two tumor types (36).

Obscurins are abundantly expressed in normal breast epithelial cells, where they localize at cell-cell junctions, the nucleus, and in cytoplasmic puncta coinciding with the Golgi membrane, but their expression is markedly diminished in breast cancer cells (33). Down-regulation of giant obscurins in non-tumorigenic MCF10A breast epithelial cells via shRNA technology conferred them with a survival advantage following exposure to DNA stress, due to reduced apoptosis, indicating that obscurins may play key roles in breast tumor suppression. Moreover, obscurin-depleted MCF10A cells acquired a mesenchymal appearance and exhibited increased cell scattering compared to control cells, which formed epithelial clusters.

The prior art is deficient in compositions and methods for prognosis and treatment of cancer. The present invention fulfills this longstanding need and desire in the art.

SUMMARY OF THE INVENTION

The present invention is directed to a method of evaluating the potential for invasiveness, metastasis, or recurrence of an epithelial cell cancer, comprising the steps of detecting giant obscurin expression in a tissue sample of tumor cells or suspected tumor cells; and assessing giant obscurin expression profile in the cells, wherein a decreased level and/or altered subcellular distribution of giant obscurins, in comparison to a control non-invasive standard or to a sample taken at a different point in time, is indicative of increased potential of at least one of the invasiveness, metastasis, or recurrence of the epithelial cell cancer.

The present invention is further directed to a method for modulating invasiveness and metastatic potential of an epithelial cell cancer cell comprising contacting cells associated with the epithelial cell cancer with a reagent that causes increased expression of giant obscurin or restoring giant obscurin activity by administering a minimal portion of giant obscurin required to suppress the tumorigenic and metastatic phenotype of cancer cells.

The present invention is further directed to an antibody raised against immunoglobulin domains 58/59 of giant obscurin proteins.

The present invention is further directed to a kit for evaluating potential for invasiveness, metastasis, or recurrence of an epithelial cell cancer, the kit comprising: a detection reagent suitable for detecting the presence of giant obscurins or an amount of the OBSCN gene product(s) in cells of a tissue sample, wherein the tissue sample includes tumor tissue of the cancer and cell tissue surrounding the tumor; and instructions for using the detection reagent to detect giant obscurins or the amount of the gene product(s) in tumor cells of the tissue sample, thereby evaluating the potential for the invasiveness, metastasis, or recurrence of the cancer based on amounts of giant obscurin or the amount of the gene product(s) in the tumor cells.

The present invention is further directed to a method for improving a response to a therapy for a cancer treatment in a subject, comprising the step of: supplementing said therapy by administering an effective amount of an agent that enhances expression of giant obscurins or restoring obscurin activity by administering a minimal portion of obscurins required to suppress the tumorigenic and metastatic phenotype of cancer cells.

Other and further aspects, features, and advantages of the present invention will be apparent from the following description of the presently preferred embodiments of the invention given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 1A is a schematic representation of giant obscurins A and B depicting their adhesion and signaling motifs. The regions used for the generation of the obscurin Ig58/59 and Ig65/66 antibodies are also denoted. Representative images of paired normal (FIG. 1B and FIG. 1D) and invasive ductal carcinoma (IDC) biopsies of stage 2 (FIG. 1C) and stage 1 (FIG. 1E); Haematoxylin & Eosin (H&E) stained tissue sections are shown in the left columns with boxed areas corresponding to regions examined under confocal optics after immunolabeling with the obscurin Ig58/59 antibody shown in middle columns and DAPI shown in right columns. Obscurins are present at the cell membrane in normal samples, where they exhibit prominent luminal distribution (FIG. 1B, arrow). The expression of obscurins is significantly reduced in IDC stage 2 biopsies with residual proteins accumulating in cytoplasmic puncta, FIG. 1C, arrowhead), but not in IDC stage 1 biopsies, where they are readily expressed at the plasma membrane (FIG. 1E).

FIGS. 2A-2E show obscurin-depleted MCF10A breast epithelial cells form mammospheres with enriched markers for cancer initiating cells. FIG. 2A shows that MCF10A cells stably transduced with obscurin shRNA-1 (right) are able to form primary mammospheres, while control cells (left) are not. FIGS. 2B-2C show the quantification of primary (FIG. 2B) and secondary (FIG. 2C) mammospheres formed by MCF10A cells stably expressing obscurin shRNA-1, compared to MCF10A cells expressing scramble control shRNA; n=3, error bars=SD, *P<0.03; t-test. FIG. 2D is a representative plot obtained from FACS analysis of primary mammospheres generated from MCF10A obscurin-KD cells, indicating that they are highly enriched in a cell population with the surface marker signature $CD44^+/CD24^-$, which is associated with stem-like properties. FIG. 2E shows that approximately 40% of cells within the MCF10A obscurin-KD mammospheres are $CD44^+/CD24^-$, compared to <1% of adherent MCF10A obscurin-KD cells, as measured by FACS; n=3, error bars=SD, *P<0.03; t-test.

FIGS. 3A-3F show that loss of giant obscurins results in disruption of adherens junctions and induction of EMT. FIG. 3A are representative immunoblots of protein lysates prepared from MCF10A cells stably transduced with obscurin shRNA-1 or scramble control shRNA using a panel of antibodies to AJ proteins. FIG. 3B-3E show the subcellular distribution of AJ proteins in obscurin-depleted (bottom) and control (top) MCF10A cells. FIG. 3F are representative immunoblots of protein lysates prepared from obscurin-KD and control MCF10A cells probed with antibodies to proteins associated with EMT. Equal loading of protein lysates was ensured by measuring protein concentration, and probing for GAPDH.

FIG. 4B are FRAP curves indicating the fraction of initial fluorescence intensity as a function of time for MCF10A cells expressing control shRNA or obscurin shRNA-1 where the time of photobleaching is indicated by the arrowhead. FIG. 4C shows the mobile fraction of LifeAct-GFP molecules for cells expressing control shRNA (n=19) or obscurin shRNA-1 (n=21); error bars=SE, **P<0.01, t-test. FIG. 4D shows the half-life of LifeAct-GFP recovery for cells expressing control shRNA or obscurin shRNA-1.

FIG. 5A is the quantification of percent (%) wound closure of MCF10A cells stably expressing scramble shRNA or obscurin shRNA-1 between 0 and 12 hours after plating on dishes coated with collagen, fibronectin, or no substrate, growing to confluency and being wounded; n=3, error bars=SD, *P<0.03; t-test. FIG. 5B is an mage of control and obscurin shRNA-1 expressing cells migrating through 3 mm wide microchannels. Arrowheads point to the cell's leading edge at the indicated time points; h: hours. FIG. 5C shows cell velocity and FIG. 5D shows chemotactic index as a function of channel width for MCF10A cells stably expressing scramble shRNA or obscurin shRNA-1; n=3, error bars=SE of at least 30 cells analyzed per condition, P<0.01 and *P<0.001; t-test. In FIG. 5E Obscurin-KD (right) and control (left) MCF10A cells were added to a matrigel-coated chamber and allowed to invade for 16 hours. Staining of invaded cells with crystal violet was followed by quantification of the % invasion of each cell population. FIG. 5F shows the % invasion of obscurin-KD cells compared to that of control cells, which was arbitrarily set to 100%; n=3, error bars=SD, and *P<0.03; t-test.

FIG. 6A are images of primary tumors formed 9 weeks post-transplantation of MCF10A Ras/Obsc shRNA-1 cells (left); all 8 mice (8/8) developed >1 $cm^3$ tumors. In contrast, 6 out of 8 (6/8) mice transplanted with MCF10A Ras/Ctrl shRNA (right) developed no tumors, and the remaining 2 out of 8 mice (2/8) developed small (<0.1 $cm^3$) tumors. In FIG. 6B gross morphology of internal organs of mice injected via the tail vein with Ras/Obsc shRNA-1 or Ras/Ctrl shRNA cells shows the presence of large tumors (arrows) in the lungs of the former but not the latter. FIG. 6C shows the quantification of the number of micrometastases present in the lungs of mice after tail vein injection of MCF10A cells expressing K-Ras and obscurin shRNA-1 or K-Ras and scramble control shRNA; n=6 mice per group, error bars=SD, *P<0.03; t-test. FIG. 6D is representative images of histological evaluation of the lungs of animals injected with Ras/Obsc shRNA-1 (left; Animal #1) and Ras/Ctrl shRNA (right; Animal #2) cells. A single lobe from each animal was fixed, stained with H&E, and examined for signs of lung micrometastases, indicated by arrows.

In FIG. 8A motility and in FIG. 8B invasion show effects following overexpression of the SH3-RhoGEF-PH cassette compared to control cells expressing empty lentivirus vector carrying the RFP tag. The SH3-RhoGEF-PH cassette targets efficiently to the cell membrane.

DETAILED DESCRIPTION OF THE PRESENT INVENTION

Figure 1A:
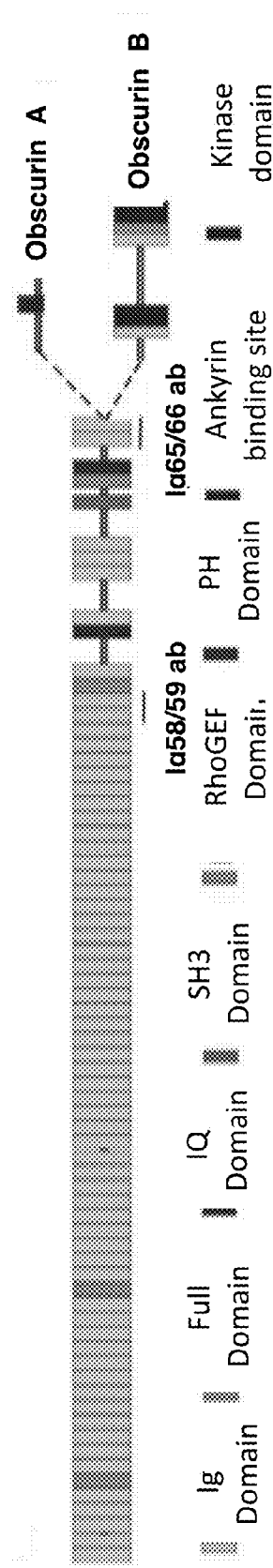
FIGS. 1A-1E show the expression profile of giant obscurins is altered in human breast cancer biopsies.

The present invention demonstrates that the expression profile of giant obscurins is dramatically altered in advanced stage human breast cancer biopsies, and that loss of giant obscurins from breast epithelial cells leads to disruption of adherens junctions (Ajs), induction of EMT, and acquisition of stem-like characteristics resulting in increased cell motility and invasion in vitro, and tumorigenicity and metastasis in vivo. Examination of the expression profile of OBSCN in the TCGA database indicated that 61.2% of all breast cancer samples analyzed had less obscurin mRNA expression. Interestingly, 95.1% of basal-like breast cancer samples (i.e. triple negative cancers) had less mRNA expression for OBSCN. The 4.9% of people with basal-like breast cancer, who did not have low expression of the obscurin mRNA did not develop metastases and did not die from breast cancer.

As used herein, the term "a" or "an", when used in conjunction with the term "comprising" in the claims and/or the specification, may refer to "one", but it is also consistent with the meaning of "one or more", "at least one", and "one or more than one". Some embodiments of the invention may consist of or consist essentially of one or more elements, method steps, and/or methods of the invention. It is contemplated that any method, compound, composition, or device described herein can be implemented with respect to any other device, compound, composition, or method described herein.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the term "about" refers to a numeric value, including, for example, whole numbers, fractions, and percentages, whether or not explicitly indicated. The term "about" generally refers to a range of numerical values, e.g., +/−5-10% of the recited value, that one of ordinary skill in the art would consider equivalent to the recited value, e.g., having the same function or result. In some instances, the term "about" may include numerical values that are rounded to the nearest significant figure.

In one embodiment of the present invention, there is provided a method for evaluating potential for invasiveness, metastasis, or recurrence of an epithelial cell cancer, comprising the steps of detecting giant obscurins expression in a tissue sample of tumor cells or suspected tumor cells; and assessing giant obscurins expression level in said cells, wherein a decreased level or altered subcellular distribution of giant obscurins in the cells, in comparison to a control non-invasive standard or to a sample taken at a different point in time, is indicative of increased potential of at least one of the invasiveness, metastasis, or recurrence of the epithelial cell cancer. Representative epithelial cell cancers include but are not limited to breast, prostate, lung, bladder, uterine, ovarian, brain, head and neck, esophageal, pancreatic, gastric, germ cell, and colorectal cancers. In this method, detecting giant obscurins expression may be by any useful technique including detecting giant obscurin proteins or detecting giant obscurins RNA by at least one selected from the group of: contacting the sample with an anti-obscurin antibody, using immunohistochemistry/immunofluorescence, hybridizing in situ a tissue or a cell using a nucleic acid probe, performing quantitative real-time polymerase chain reaction, immunoblotting an electrophotogram, and using a detection reagent. Preferably, the giant obscurin proteins have a size of at least about 700 kDa to 870 kDa and the antibody is directed against the Ig58/59 domains of giant obscurins.

In another embodiment of the present invention, there is provided a method for modulating invasiveness and metastatic potential of an epithelial cell cancer cell comprising contacting cells associated with the epithelial cell cancer with a reagent that causes increased expression of giant obscurins or restoring or improving giant obscurin activity by ectopic expression of a mini-obscurin. Representative examples of a reagent that causes increased expression of giant obscurin include but are not limited to a low molecular weight drug; a vector carrying a gene or a portion thereof encoding a mini-obscurin protein; and a naked nucleic acid encoding this protein. Most preferably, the vector is the SH3-RhoGEF-PH cassette or the RhoGEF motif alone. The suppressive effect of the RhoGEF motif alone would be valuable for gene therapy due to its even smaller size ~20 KDa compared to the SH3-RhoGEF-PH cassette which is ~45 kDa. Representative examples of epithelial cell cancers include but are not limited to breast, prostate, lung, bladder, uterine, ovarian, brain, head and neck, esophageal, pancreatic, gastric, germ cell, and colorectal cancers.

In yet another embodiment of the present invention, there is provided an antibody raised against immunoglobin domains 58/59 of obscurin proteins.

In yet another embodiment of the present invention, there is provided a kit for evaluating potential for invasiveness, metastasis, or recurrence of an epithelial cell cancer, the kit comprising: a detection reagent suitable for detecting the presence of giant obscurins or an amount of the gene product(s) of a gene encoding giant obscurins in cells of a tissue sample, wherein the tissue sample includes tumor tissue of the cancer and cell tissue surrounding the tumor; and instructions for using the detection reagent to detect giant obscurins or the amount of the gene product in tumor cells of the tissue sample, thereby evaluating the potential for the invasiveness, metastasis, or recurrence of the cancer based on the amounts of giant obscurins or the amount of the gene product(s) in the tumor cells. The instructions may include statistical correlations for evaluating the expression of a low amount or altered distribution of giant obscurins in the tumor as an indication of a greater likelihood that the tumor is invasive or has greater potential for the invasiveness, metastasis, or recurrence, and a high amount of giant obscurins in neighboring epithelial cells or the fibroblasts surrounding the tumor as an indication that the tumor is non-invasive, or has less potential for the invasiveness, metastasis, or recurrence. Preferably, the detection reagent is an antibody that specifically binds to and/or is raised against giant obscurins domains Ig58/59.

In yet another embodiment of the present invention, there is provided a method for improving a response to a therapy for a cancer treatment in a subject, comprising the step of administering an effective amount of an agent that enhances the expression of giant obscurins or improving giant obscurin activity by ectopic expression of a mini-obscurin. Representative examples of a cancer include neuroblastoma, lung cancer, pancreatic cancer, skin cancer, hematological neoplasms, breast cancer, brain cancer, colon cancer, follicular lymphoma, bladder cancer, cervical cancer, endometrial cancer, esophageal cancer, gastric cancer, head and neck cancer, multiple myeloma, liver cancer, lymphomas, oral cancer, osteosarcomas, ovarian cancer, uterine leiomyosarcoma, uterine leiomyomas, endometriomas, endometriosis, uterine papillary serous carcinomas, prostate cancer, testicular cancer, or thyroid cancer. Representative examples of a cancer therapy which may be improved by this method include, but are not limited to, surgery, chemotherapy, radiotherapy, thermotherapy, immunotherapy, hormone therapy, and laser therapy. For example, the therapy may be treatment with one or more of 13-cis-retinoic acid, an antibody, a cytokine, a platinum compound, an alkylating agent, an antimetabolite, vinca alkaloid, or a DNA topoisomerase inhibitor. Representative examples of a cytokine are GM-CSF, IL-2 or GM-CSF/IL-2. Representative examples of a platinum compound are carboplatin or cisplatin. Representative examples of a alkylating agent are cyclphosphamide or melphalan.

Representative examples of a antimetabolite are an antitumor antibiotic or an anthracycline antiobiotic. A representative example of an antibiotic is doxorubicin. A representative example of a vinca alkaloid is vincristine. A representative example of a DNA topoisomerase inhibitor is topeotecan or etoposide.

The following example(s) are given for the purpose of illustrating various embodiments of the invention and are not meant to limit the present invention in any fashion.

Example 1

Materials

Unless otherwise noted, all chemicals were purchased from Sigma-Aldrich (St. Louis, Mo., USA).

Example 2

Cell Culture

MCF10A stable clones expressing obscurin shRNA-1, obscurin shRNA-2 or control shRNA plasmids were generated and maintained as described (33). MCF10A stable clones expressing K-Ras (provided by Drs. M. Vitolo and S. Martin, UMSOM) were tranfected with obscurin shRNA-1, obscurin shRNA-2, or scramble control shRNA using LIPOFECTAMINE 2000 (Invitrogen); 1.5 mg/ml puromycin was added to the medium to select for stably transfected cells 3 days post-transfection.

Example 3

Antibodies

The antibodies used were as follows; rabbit polyclonal: obscurin-COOH (600 ng/ml) (28), obscurin-Ig58/59 (2 mg/ml) that was generated using a mouse GST-Ig58/59 fusion protein (amino acids 5218-5390, accession number: NP_954603), plakoglobin (11146-1-AP, Proteintech Group Inc, Chicago, Ill., USA), myosin IIA (3403, Cell Signaling Technology, Danvers, Mass., USA), twist (sc-15393, Santa Cruz Biotechnology Inc, Santa Cruz, Calif., USA), claudin-1 (4933, Cell Signaling Technology), and ZO-1 (5406, Cell Signaling Technology); mouse monoclonal: β-catenin (sc-7963, Santa Cruz Biotechnology Inc), connexin-43 (13-8300, Invitrogen), p120 catenin (ab11508, Abcam, Cambridge, Mass., USA), GAPDH (AM4300, Applied Biosystems, Carlsbad, Calif., USA); rabbit monoclonal: E-cadherin (3195, Cell Signaling Technology), α-catenin (ab51032, Abcam), vimentin (5741, Cell Signaling Technology), and slug (9585, Cell Signaling Technology).

Generation and Purification of the Obscurin 1q58/59 Antibodies

Ig domains 58/59 were used as antigen for the immunization of rabbits. The sequence of the antigen (K5281-L5462, accession number A2A AJ9) is: KNTVLRGLENVDALEGGEALFECQLSQPEVAAHTWLLDDEPVHTSEKVEVVYFENGLRHLLLL KNLKPQDSCRVTFLAGDVVTSAFLTVRGWRLEVLEPPHDASVKAGMQVRFTCILSEAVPVGEA TWYINGAAIQPDDTDWTVTTDGSHHALTLSNAQPQHAGEVTFAARDAVASARLSVL (SEQ ID NO: 27). The antigen was conjugated to Glutathione-S-Transferase (GST) to allow affinity purification following bacterial expression.

Purification of Obscurin 1q58/59 Antibody

The crude immunized rabbit serum was dialyzed in 3 L of PBS+1 mM sodium azide overnight at 4° C., with 2 changes of solution. The dialyzed serum was incubated with a GST-conjugated cyanogen bromide column overnight. The collected flow-through was subsequently incubated with GST-ObIg5859 antigen conjugated to cyanogen bromide beads overnight at 4° C. The column was then washed extensively with PBS/1 mM sodium azide solution, and the antibody was eluted in elution buffer (0.1 M glycine, 0.5 M NaCl, pH, 2.4). Each elution fraction was about 400-800 ul, and was immediately neutralized with 100 ml of 1M Tris-HCl, pH 8.15.

Example 4

Human Samples and Immunohistochemistry

Human breast cancer tumor microarray slides containing paraffin embedded invasive ductal breast carcinoma and age, sex, and stage matched normal tissue were examined (US Biomax Inc, Rockville, Md., USA). In particular, 10 biopsies of invasive ductal carcinoma (IDC) grade-1, 35 biopsies of IDC grade-2, 6 biopsies of IDC stage-3, and 3 biopsies of invasive lobular carcinoma grade-2 were analyzed. Tissue sections were deparaffinized in xylene, rehydrated with graded alcohol washes, and subjected to antigen retrieval using 10 mM sodium citrate. Following washes in TBS (Tris borate saline) containing 0.025% Triton X-100 (TBST), sections were blocked with 10% Normal Goat Serum and 1% Bovine Serum Albumin (BSA) in TBS for 2 hours. Slides were incubated with the rabbit polyclonal obscurin Ig58/59 antibody diluted in TBS containing 1% BSA and incubated overnight at 4° C. Sections were subsequently washed with TBST and incubated for 2 h with goat anti-rabbit Alexa Fluor-568 secondary antibody (LifeTechnologies, Carlsbad, Calif., USA). Following extensive washes in TBST, slides were mounted with PROLONG Gold Antifade Reagent with DAPI (LifeTechnologies), and analyzed in a LSM510 confocal microscope (Carl Zeiss) under 40× magnification.

Example 5

Generation of Protein Lysates and Western Blotting

Age, stage, and sex matched human normal and breast cancer biopsies were commercially obtained (ILSbio, Chestertown, Md., USA). Tissue homogenates were prepared on ice with a hand-homogenizer in radioimmuno-precipitation assay (RIPA) buffer supplemented with a cocktail of protease inhibitors (Roche, Mannheim, Germany) and phosphatase inhibitors (200 nM Imidazole, 100 mM Sodium Flouride, 115 mM Sodium Molybdate, 100 mM Sodium Orthovanadate, 400 mM Sodium Tartrate Dihydrate, 100 mM p-Glycerophosphate, 100 mM Sodium Pyrophosphate, and 10 mM EGTA), as described (1). Protein lysates were electrophoresed on SDS NUPAGE gel (Invitrogen), transferred to nitrocellulose membranes, and probed with primary antibodies as specified. Alkaline phosphatase-conjugated anti-mouse or anti-rabbit IgG (1:3,000; Jackson ImmunoResearch, West Grove, Pa., USA) were used, and immunoreactive bands were visualized with a chemiluminescence detection kit (Applied Biosystems). The relative abundance of immunoreactive bands was determined with densitometry using Image J software.

Example 6

Mammosphere Culture

Single MCF10A cells stably transduced with obscurin shRNA-1, obscurin shRNA-2 or scramble control shRNA were plated in ultralow attachment plates (Corning, Lowell, Mass., USA) at a density of 10,000 viable cells/ml in serum-free growth media (DMEM/F12 with GlutaMAX™), supplemented with insulin (10 μg/ml), hydrocortisone (0.5 μg/ml), cholera toxin (100 ng/ml), epidermal growth factor (20 ng/ml), 1% penicillin-streptomycin and puromycin (1.5 μg/ml). Cultures were supplemented with serum-free growth media every other day for 14 days at which time point, primary spheres were measured and those >100 Lm were counted as tumor spheres. Mammospheres were then collected by gentle centrifugation (800 rpm) and dissociated enzymatically (2 min in 0.25% trypsin-EDTA (1×); Invitrogen) and mechanically using a sterile pipette. To evaluate secondary mammosphere forming efficiency, dissociated cells obtained from primary mammospheres were seeded at 1 cell per well into 96-well ultralow attachment plates (Corning). Cells were grown as described above for 14 days and the number of secondary mammospheres per well with sizes of 50-100 mm was counted. Sphere-forming efficiency (SFE) was calculated as the number of spheres formed divided by the original number of single cells seeded, and expressed as percentage.

Example 7

Fluorescence Activated Cell Sorting (FACS)

CD24 and CD44 expression was analyzed in MCF10A cells stably expressing obscurin shRNA-1 grown in a monolayer or in mammospheres. Cells were dissociated following incubation in trypsin/EDTA combined with manual trituration using a Pasteur pipette and pelleted by centrifugation at 1000 g for 10 min. Cells were resuspended in phosphate-buffered saline with 0.1% BSA (wt/vol). Cell suspensions were incubated with mouse anti-human CD44-APC antibody (BD Pharmigen, San Jose, Calif., USA) and mouse anti-human CD24-PE antibody (BD Pharmigen) for 30 min at 4° C. All flow cytometry assays were performed using a BD FACSCalibur and data analysis was accomplished using BD CellQuest Pro software (BD Biosciences).

Example 8

Immunofluorescence Combined with Confocal Microscopy

Cells were fixed with freshly prepared 3.7% paraformaldehyde, permeabilized with 0.25% Triton X-100 in PBS containing 1 mg/ml BSA (PBS/BSA) and blocked with 5% normal goat serum. Cells were subsequently incubated overnight at 4° C. with primary antibodies as specified in the text, counterstained with goat anti-rabbit Alexa Fluor-568 or goat anti-mouse Alexa Fluor-568 IgG (LifeTechnologies) at a 1:200 dilution, and analyzed in a LSM510 confocal microscope (Carl Zeiss) under 63× magnification.

Example 9

RNA Isolation, cDNA Synthesis, and PCR Amplification

Total RNA was isolated from cultured cells with the TRIzol reagent (Invitrogen) and reverse-transcribed using the SuperScript III First-Strand Synthesis Kit (Invitrogen). PCR amplification was performed with GoTaq Green Master Mix (Promega), using the primer sets listed in Table 1. All amplicons were purified and sequenced.

TABLE 1

| Primer Name | Sequence |
| --- | --- |
| E-cadherin Forward | ATCAGGCCTCCGTTTCTG (SEQ ID No: 1) |
| E-cadherin Reverse | GCAGCTGATGGGAGGAAT (SEQ ID No: 2) |
| β-catenin Forward | GAAAATCCAGCGTGGACAATG (SEQ ID No: 3) |
| β-catenin Reverse | ACGCATGATAGCGTGTCT (SEQ ID No: 4) |
| α-catenin Forward | GTGGGGCTGCCTTGATG (SEQ ID No: 5) |
| α-catenin Reverse | AATTGCACCAGCTGTGCG (SEQ ID No: 6) |
| p120 catenin Forward | CAGCTGCTATGCGGGT (SEQ ID No: 7) |
| p120 catenin Reverse | ACCTCCTTCTGGTTGCTCT (SEQ ID No: 8) |
| N-cadherin Forward | CCTGCTTCAGGCGTCTGTAG (SEQ ID No: 9) |
| N-cadherin Reverse | CTGCCTTTGTAGGTGGCCAC (SEQ ID No: 10) |
| Vimentin Forward | GGCAGAAGAATGGTACAAATCC (SEQ ID No: 11) |
| Vimentin Reverse | CTTCCAGCAGCTTCCTGTAG (SEQ ID No: 12) |
| Slug Forward | CTCCATTCCACGCCCA (SEQ ID No: 13) |
| Slug Reverse | AATGGGTCTGCAGATGAGC (SEQ ID No: 14) |
| Twist Forward | GAGTCCGCAGTCTTACGAGG (SEQ ID No: 15) |
| Twist Reverse | CTGCCCGTCTGGGAATCACT (SEQ ID No: 16) |
| Claudin-1 Forward | GCAGCACATTGCAAGCAACC (SEQ ID No: 17) |
| Claudin-1 Reverse | CGCTGGAAGGTGCAGGT (SEQ ID No: 18) |
| ZO-1 Forward | CACCAAGTACTGAGGCAGC (SEQ ID No: 19) |
| ZO-1 Reverse | TGGACTCTGCAGGCTTGG (SEQ ID No: 20) |
| Plakoglobin Forward | CAGTAGCCACGATGGAGGT (SEQ ID No: 21) |
| Plakoglobin Reverse | CGACGCCTCCTTCTTCG (SEQ ID No: 22) |
| Connexin-43 Forward | AGCGCCTTAGGCAAACTCCT (SEQ ID No: 23) |
| Connexin-43 Reverse | ATCAGCAAGAAGGCCACCTC (SEQ ID No: 24) |

Example 10

Fluorescence Recovery after Photobleaching (FRAP)

Fluorescence recovery after photobleaching was used to analyze actin molecule dynamics in living cells. Cells were transfected with LifeAct-GFP using LIPOFECTAMINE 2000 (Invitrogen, Grand Island, N.Y.) and re-plated onto collagen-coated glass coverslips with PDMS barriers to retain cell media. After allowing the cells to adhere and form a monolayer for 24 hours, coverslips with cells were positioned on the stage of a Zeiss LSM 510 META laser scanning confocal microscope (Carl Zeiss Microlmaging, Thornwood, N.Y.). A circular region of interest at cell-cell borders with 4 mm diameter was photobleached using a 488 nm laser at 100% power. Images were captured at maximum rate (2.15 second intervals) before and after photobleaching using a 63x/1.4 NA oil objective and LSM software (version 4.2). Image J was used to analyze fluorescence intensity in the photobleached region as a function of time using the "Plot z-axis profile" function. In non-fluorescent regions of the image, background fluorescence as a function of time was measured to be zero using the same method. At least 20 images of cell-cell borders per cell group were analyzed. Intensity within the photobleached region was normalized such that an intensity value of 1 corresponded to the mean fluorescence intensity of 5 pre-bleach images, while an intensity value of 0 corresponded to the fluorescence intensity just after photobleaching. Data for fluorescence intensity as a function of time (l(t)) were fit to the following standard equation for binding kinetics: $I(t)=I_{final}(1-e^{-\tau t})$, where $I_{final}$ is the mobile fraction of actin molecules, and $\tau$ is related to the half-life ($\tau_{1/2}$) by the following formula:

$$\tau_{1/2} = -\frac{\ln(0.5)}{\tau}.$$

Example 11

Migration in 2Dimensional Substratum Using LifeAct-GFP

To image actin dynamics live during cell migration, MCF10A cells were transfected with LifeAct-GFP using LIPOFECTAMINE 2000. Two days after transfection, cells were plated onto type 1 collagen-coated glass coverslips (20 µg/mL in PBS), allowed to adhere overnight, and imaged at 2-min intervals for ~4 h using an automated Nikon fluorescence microscope (20x objective).

Example 12

Wound Healing and Invasion Assays

Wound healing was measured by growing confluent cell monolayers as described above in six-well tissue culture dishes (Corning) that were uncoated or pre-coated with human fibronectin (BD Biosciences, Bedford, Mass., USA) or collagen type I (BD Biosciences). A scrape was made through the monolayer with a sterile plastic pipette tip and fresh media was added. Images were taken with an inverted microscope (10x objective) at time zero and after a 12 hour incubation period at 37° C., 5% $CO_2$. Migration was expressed as the average of the difference between the measurement at time zero and 12 hours obtained from 3 independent experiments.

Invasion was measured by adding 250,000 cells suspended in 0.5 ml growth media to the upper chamber of a Matrigel-coated Invasion Chamber (BD Biosciences). The lower chamber contained growth media with 10% FBS. The inserts were incubated at 37° C., 5% $CO_2$ for 16 hours. At the end of the 16 hour incubation period, the cells that had invaded in the lower chamber were fixed and stained with 0.5% crystal violet in 20% methanol. The number of invaded cells was quantified by counting at least 10 random fields from 3 independent experiments under an inverted light microscope (Olympus IX51) with a 10x objective.

Example 13

Fabrication of the Microchannel Device

The microchannel device was fabricated by standard lithography as described (4, 9, 26, 43). Briefly, SU-8 photoresist was spin coated onto a silicon wafer to a thickness of 10 µm and cross-linked by exposure to UV light through a photomask with variable transparent separation distances, ranging from 3-50 µm. Developer was used to remove non-crosslinked photoresist. This process was repeated with a 50 µm-thick layer of SU-8 and a second mask containing two 400 µm-wide channels spaced 200 µm apart. Polydimethylsiloxane (PDMS) was prepared at a 10:1 ratio with curing agent poured over the silicon master, and degassed in a vacuum chamber for 2 hours. The PDMS was baked at 85° C. for 1 hour, peeled off the master, cut to appropriate size, and pierced to form inlet and outlet ports. The PDMS device and 75 mm glass coverslips were treated with oxygen plasma for 3 minutes and irreversibly sealed together upon contact, forming 4-walled microchannels. The surface of the PDMS microchannels was functionalized by adding type-1 collagen (20 µg/mL in PBS) to the ports of the device and incubating for 1 hour at 37° C.

Example 14

Microchannel Seeding and Cell Migration

Cells were trypsinized, resuspended in serum-free media to neutralize the trypsin and subsequently washed in serum-free media. A suspension of $1 \times 10^5$ cells was added to the inlet port, and cells were transported along the seeding channel by pressure-driven flow. Within 5 minutes, the cell suspension was removed and replaced with 50 µl of serum-free media, which was also added to the upper inlets. Serum-containing media was added to the top-most inlet port, thus forming a chemoattractant gradient. A thin layer of ($CO_2$-permeable) PDMS was placed over the chamber inlet and outlet ports to prevent media evaporation during imaging. Chambers were placed in an enclosed, humidified microscope stage at 5% CO2 and 37° C. (TIZ, Tokai Hit Co., Japan). Phase contrast time-lapse images were captured at 10 minute intervals for 14 hours on an inverted Nikon microscope (10x objective) at multiple stage positions via stage automation (Nikon Elements, Nikon, Japan). Cell x,y position within the microchannel was identified as the midpoint between the poles of the cell body and tracked as a function of time using ImageJ (NIH, Bethesda, Md.). Cell velocity and chemotactic index were computed using a custom-written Matlab program (The MathWorks, Natick, Mass.). Instantaneous cell velocity was calculated by dividing each interval displacement by the time interval (10 minutes), and the mean velocity for a given cell was computed by averaging instantaneous velocities for all time intervals. Chemotactic index was calculated by dividing the end-to-end displacement by the total path length of the cell.

The reported velocity and chemotactic index for each condition is the mean of the pooled cells from 3 independent experiments.

Example 15

Mice

All experimental procedures complied with guidelines provided by the Office of Laboratory Animal Welfare at the National Institutes of Health, and all protocols were approved by the Johns Hopkins University Animal Care and Use Committee. Adult NSG mice (male and female) were used as tumor recipients for mouse experiments (Stock 5557, Jackson Labs).

Example 16

Subcutaneous Injections

Suspensions of $2\times10^6$ cells in 100 µl matrigel were injected subcutaneously into the flank of mice (8 per experimental group). Tumors were measured in three dimensions with an electronic digital caliper. Tumor volume was calculated as described (L)×(W)×(H)×p/6 (32). Animals were euthanized 9 weeks post-implantation.

Example 17

Tail Vein Injections

Mice (6 per experimental group) were injected with $1\times10^6$ cells in a volume of 50 µl of culture media via the tail vein. Animals were euthanized 9 weeks post-injection (15).

Example 18

Histopathology of Lung Tissue

Lungs and other tissues were examined visually for lesions and metastatic foci. Lung samples for pathology were fixed in 10% buffered formalin. The left lung lobe was used for hLINE analysis and the remaining lobes were embedded in a single cassette and sectioned for histopathological analysis of metastastatic foci (37, 39). Samples were embedded in paraffin, sectioned at 5 µm, and stained with hematoxylin and eosin using standard techniques. Primary tumors were scored 0-3 based on size and 0-3 based on extent of necrosis in each tumor by histopathology. Scores were totaled and individual tumors were graded as follows: grade 1=total score of 1-2; grade 2=total score of 3-4; and grade 3=total score of 5-6. Tissue collection, histopathology analysis, and grading were performed by a pathologist (DLH).

Example 19

Quantification of Human Long Interspersed Nuclear Element-1 (hLINE-1) Gene

DNA was extracted from mouse tissue as described (13, 37) using the DNeasy blood and tissue kit (Qiagen, Valencial, Calif., USA) in a sterile biological safety cabinet to minimize the risk of human DNA contamination. Elutions were analyzed via qPCR as reported previously (39). Briefly, qPCR was performed in 15 ml volume with the following components: 7.5 ml iQ SYBR Green Supermix (Bio-rad, Hercules, Calif., USA), 1.5 ml of each 10 µM forward (5'-TCACTCAAA GCCGCTCAACTAC-3') (SEQ ID No: 25) and reverse (5'-TCTGCCTTCATTTCGTTATGTACC-3') (SEQ ID No: 26) primers, and 4.5 µl of purified DNA. The reaction was monitored on a MyiQ Real Time PCR Detection System (Bio-rad) with the following cycles: (94° C., 2 min)×1, (94° C., 10 s; 67° C., 15 s; 70° C., 15 s)×3, (94° C., 10 s; 64° C., 15 s; 70° C., 15 s)×3, (94° C., 10 s; 61° C., 15 s; 70° C., 15 s)×3, and (94° C., 10 s, 59° C., 15 s; 70° C., 15 s)×35. Threshold cycle number was calculated using Bio-Rad iQ5 software. Dilutions of human DNA purified from MCF10A breast epithelial cells were included in each plate to serve as standards.

Example 20

Reproducibility and Statistics

All experiments were performed in triplicates a minimum of three times, unless otherwise noted, and data are presented as mean values of independent measurements. Statistical significance was assessed using Student's t-test.

Example 21

Comparison of Obscurin Ig58/59 Antibodies to Other Obscurin Antibodies

In addition to obscurin Ig58/59 antibodies, four other obscurin antibodies were also examined in immunohistochemistry/immunofluorescence assays with human breast cancer biopsies, including $\alpha$-NH$_2$, $\alpha$-ABD, $\alpha$-COOH, and $\alpha$-Kinase (Ackermann M. A. et al, PLOS One, 2014). These non-Ig58/59 antibodies failed to reliably and consistently detect giant obscurins. These antibodies were not compatible with the required antigen retrieval and ficin treatment of the biopsies. The $\alpha$-NH$_2$ antibodies provided weak staining of obscurins and the $\alpha$-ABD, the $\alpha$-COOH, and the $\alpha$-Kinase antibodies detected various smaller, uncharacterized forms of obscurins in normal human tissue, and potentially truncated or degraded forms of obscurins in cancerous human tissue, thus yielding confusing results. Thus, the present invention demonstrated that the $\alpha$-Ig58/59 antibody combined with immunohistochemical/immunofluorescent staining provided the most specific and consistent staining for giant obscurins in human tissue sections.

Example 22

Expression Profile of Giant Obscurins in Human Breast Cancer Biopsies

Figure 1B:
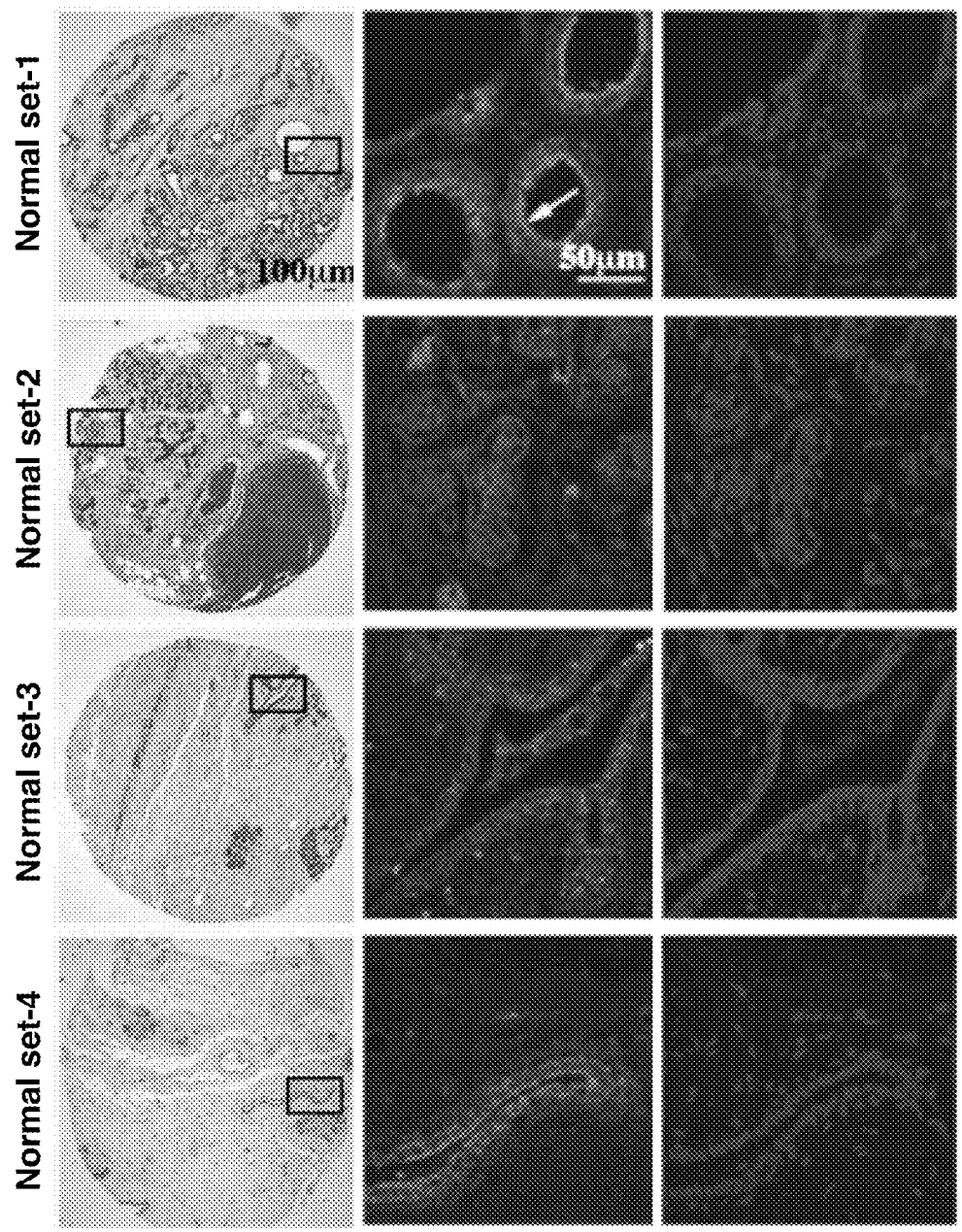
Figure 1C:
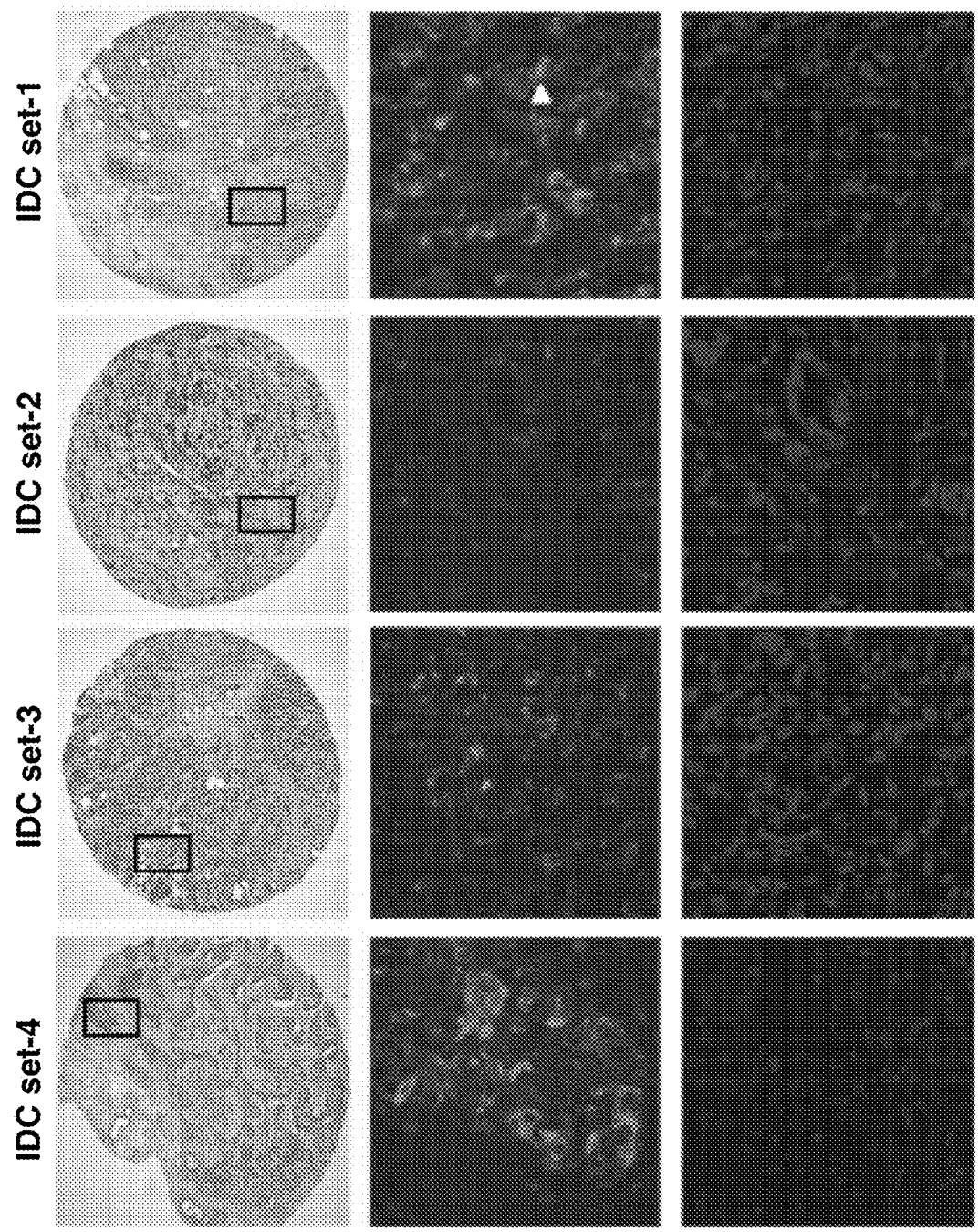
Figure 1D:
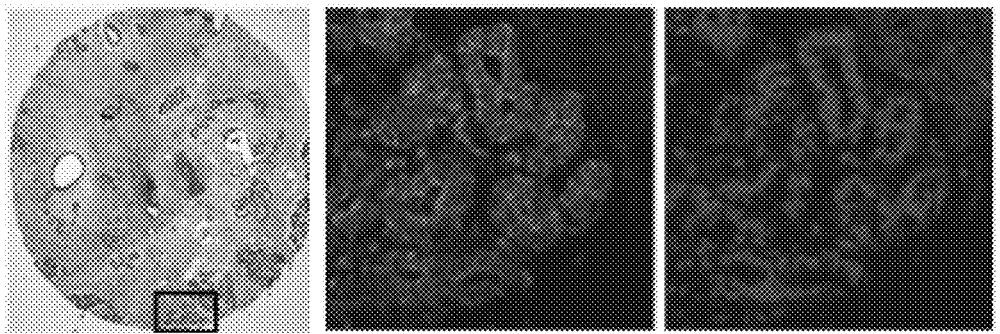
Figure 1E:
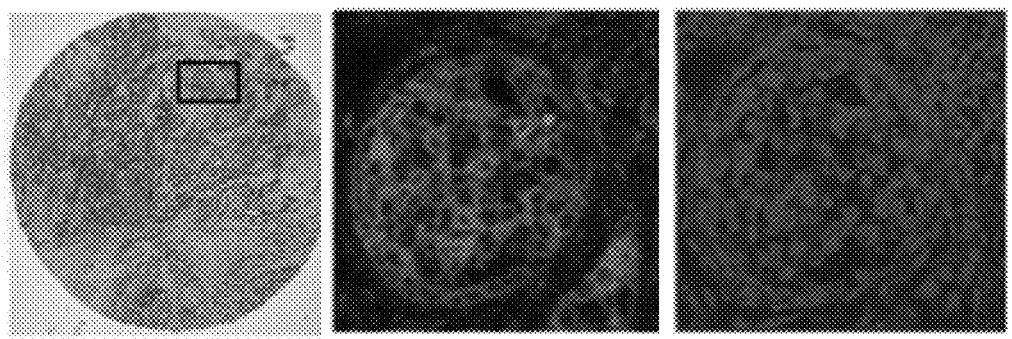

Fluorescent immunohistochemical methods and confocal imaging to investigate the expression profile of giant obscurins in human biopsies of invasive ductal carcinoma, which accounts for >80% of metastatic breast cancer, compared to normal matched samples, using an antibody that recognizes epitopes present in Ig domains 58 and 59 of obscurins A and B (FIG. 1A). Obscurins were expressed in the ductal and lobular epithelium of normal breast tissue, where they exhibit membrane localization, with prominent concentration on the luminal side of epithelial cells in larger ducts and lobules (FIG. 1B, arrow). In contrast, they are nearly absent from matched invasive ductal breast cancer tissue of grade 2 or higher with residual obscurins accumulating in large cytoplasmic puncta throughout the tumor mass (FIG. 1C, arrowhead). Interestingly, invasive ductal breast cancer samples of grade 1 maintain membrane localization of obscurins similar to paired normal breast tissue samples (FIGS. 1D-1E).

To further elucidate changes in the expression levels of giant obscurins in human biopsies, western blotting was employed using an antibody that detects epitopes present in Ig domains 65 and 66 (FIG. 1A). Analysis of protein homogenates prepared from age-, sex-, and stage-matched normal and invasive ductal or infiltrating lobular carcinomas revealed a dramatic reduction in the amounts of giant obscurins A and B in the carcinoma specimens. Moreover, down-regulation of an additional immuno-reactive band was consistently observed with a calculated molecular mass of ~600 kDa, that potentially corresponds to a novel giant obscurin isoform. In agreement with this, the complete sequence of a novel obscurin isoform of human origin was recently deposited in the Ensembl database (Accession Number: ENSP00000355668) with a predicted molecular mass of ~611 kDa that starts in Ig31. Homogenates prepared from cancer biopsies of either ductal or lobular origin contained smaller immunoreactive bands ranging in size between 300-90 kDa, which were absent from homogenates prepared from paired normal samples. These smaller obscurin forms may be novel, still uncharacterized, obscurin proteins or degradation products of giant obscurins due to the presence of missense or nonsense mutations in the OBSCN gene (3, 36, 41). Collectively, these findings indicate that the expression levels of giant obscurins were markedly diminished in breast cancer biopsies of both ductal and lobular origin, whereas residual obscurins, potentially representing mutant and/or truncated forms of giant obscurins, accumulate in large cytoplasmic puncta.

Example 23

Figure 2A:
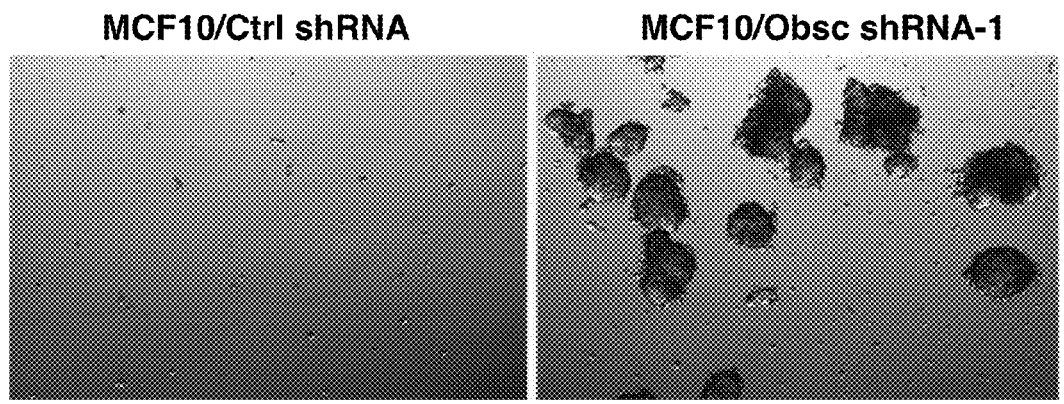
Figure 2B:
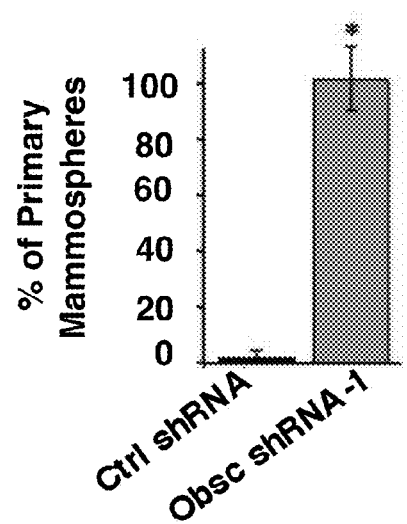
Figure 2C:
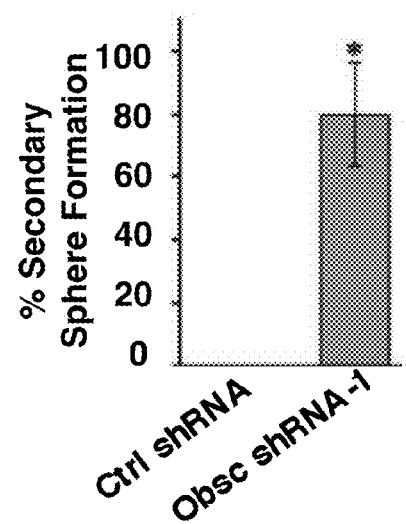

Obscurin-Depleted Breast Epithelial Cells Form Mammospheres with Stem-Like Characteristics To examine the role of giant obscurins in breast epithelium, stable MCF10A obscurin-depleted cell lines were generated using shRNA constructs (shRNA 1-4) targeting different sequences within the common $NH_2$-terminus and middle portion of giant obscurins A and B (33). Depletion of giant obscurins from MCF10A cells bestows them with a survival advantage following exposure to DNA damaging agents (33). Whether loss of giant obscurins also affected cell growth and proliferation was also examined. Stable clones of MCF10A breast epithelial cells depleted of giant obscurins using shRNA-1 were allowed to form mammospheres in serum-free media and ultra-low attachment plates. Obscurin-depleted MCF10A cells formed robust mammospheres greater than 100 μm, while control cells stably transduced with scramble shRNA failed to do so (FIGS. 2A-2B). MCF10A cells depleted of giant obscurins using shRNA-2 exhibited similar mammosphere forming efficiency. To further investigate their self-renewing capabilities, primary mammospheres were dissociated and plated as single cells in 96-well culture dishes under similar culture conditions. Approximately 80% of obscurin-depleted MCF10A cells formed secondary mammopsheres ranging in size between 50-100 μm upon passaging (FIG. 2C).

Given that cultured mammospheres are often enriched in breast cancer initiating cells containing the cell surface signature $CD44^+/CD24^-$ (35), the presence and relative abundance of $CD44^+/CD24^-$ cells was examined in MCF10A obscurin-deficient primary mammospheres using flow cytometry. Approximately 40% of obscurin-knockdown (KD) cells stained positive for CD44 and negative for CD24 compared to <1% of adherent obscurin-KD cells grown in a monolayer (FIGS. 2D-2E). Thus, loss of giant obscurins from breast epithelial cells promotes cell growth and acquisition of stemness.

Example 24

Down-Regulation of Giant Obscurins in Breast Epithelial Cells Disrupts Adherens Junctions and Results in Epithelial to Mesenchymal Transition (EMT)

Figures 3B, 3C, 3D, 3E:
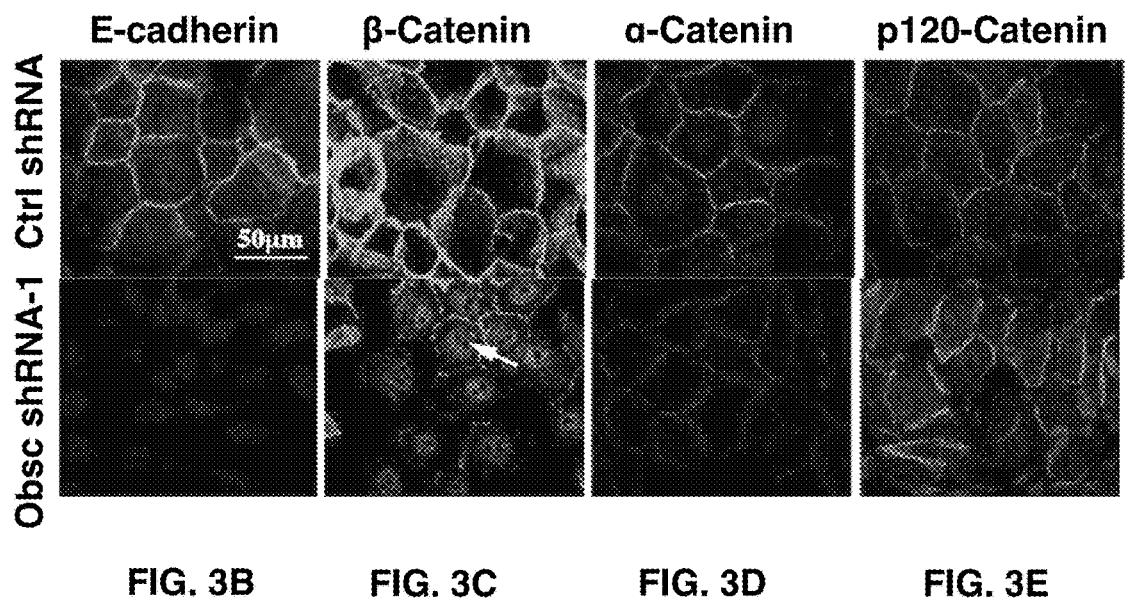

Depletion of giant obscurins from MCF10A cells results in acquisition of a mesenchymal phenotype and increased cell scattering (33), both of which are associated with altered cell junctions (17). The expression profile of various proteins within cell-cell junctions of MCF10A cells stably expressing obscurin shRNA-1 was analyzed. A dramatic decrease was observed in the amounts of E-cadherin (98%), β-catenin (82%) and α-catenin (38%), while the levels of p120 catenin were significantly increased (114%) (FIG. 3A). Similar results were obtained with MCF10A cells stably transduced with obscurin shRNA-2. Consistent with the immunoblot analysis, immunostaining of obscurin-depleted MCF10A cells revealed a dramatic reduction of E-cadherin, β-catenin, and α-catenin from cell-cell contacts (FIG. 3B-3E). While residual E-cadherin assumed a homogeneous cytosolic distribution, residual β- and α-catenin exhibited discontinuous distributions at cell-cell contacts. Notably, remaining b-catenin also showed nuclear accumulation (FIG. 3C right, arrow). In contrast, p120 catenin localized at cell-cell junctions similarly to control cells. Collectively, these results indicate that loss of giant obscurins markedly alters both the expression levels and subcellular distribution of proteins within AJs.

Figure 3F:
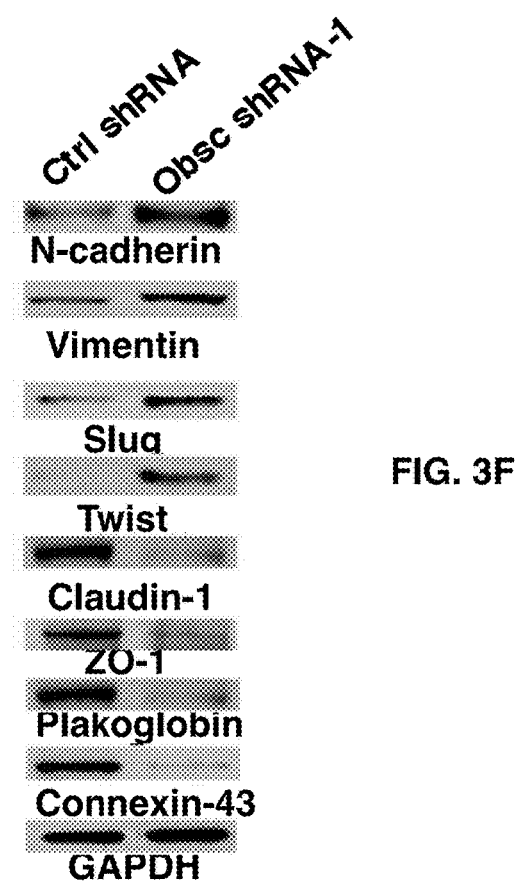

Whether MCF10A cells depleted of giant obscurins via obscurin shRNA-1 undergo EMT was examined. There was a significant increase in the amounts of major mesenchymal proteins intimately associated with EMT, such as N-cadherin (175%) and vimentin (125%) (FIG. 3F). Consistent with this, expression levels of transcriptional regulators of EMT, including Slug (435%) and Twist (394%), were elevated (FIG. 3F). In contrast, the amounts of junctional epithelial proteins, like claudin-1 (100%), zona occludens-1 (ZO-1; 62%), connexin-43 (82%) and plakoglobin (88%) were drastically reduced (FIG. 3F). Analysis of the expression levels of the same battery of proteins in MCF10A cells stably transduced with obscurin shRNA-2 yielded similar results. The concurrent increase in the expression levels of mesenchymal proteins and decrease in the expression levels of epithelial junctional proteins indicate that loss of giant obscurins induces EMT in breast epithelial cells.

Example 25

Loss of Giant Obscurins Increases F-Actin Dynamics at Cell-Cell Contacts

Figure 4A:
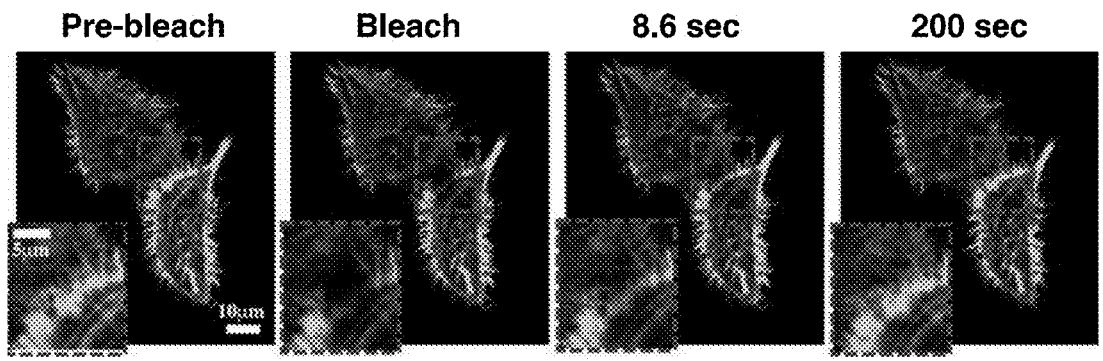
FIGS. 4A-4D illustrate that Obscurin-KD MCF10A cells show increased actin dynamics at cell-cell borders, as measured by FRAP. LifeAct-GFP was expressed in MCF10A cells stably transduced with obscurin shRNA-1 (FIG. 4A) or control shRNA. A circular region of 4 μm in diameter at a cell-cell junction was photobleached, and LifeAct-GFP expression was imaged during fluorescence recovery at different time points. The dotted square regions correspond to the zoomed images shown in insets.
Figure 4B:
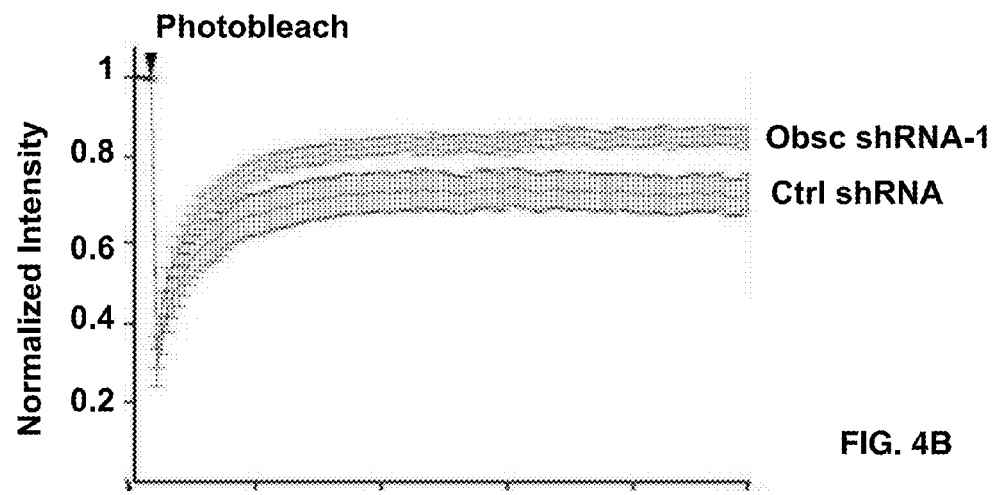
Figure 4C:
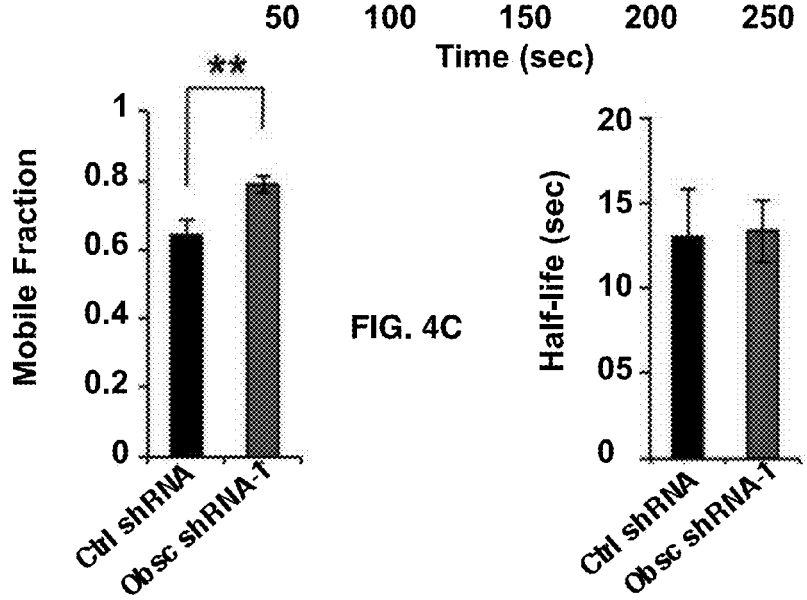
Figure 4D:
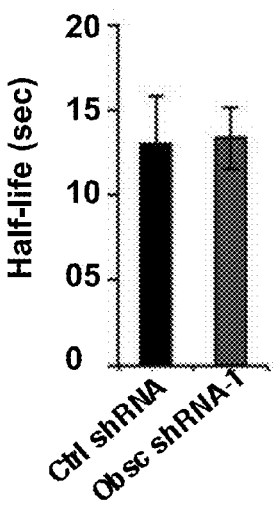

Given the disruption of the adherens junctions in conjunction with the mesenchymal phenotype that obscurin-depleted MCF10A cells acquire, whether there were changes in the distribution and dynamics of actin filaments was assessed. Use of phalloidin staining to visualize actin localization in obscurin-KD cells revealed the presence of filopodia-like protrusions, enriched in actin filaments, emanating from the edges of the cells and such membrane protrusions were nearly absent in control cells, which contained actin bundles surrounding the circumference of the cells. In light of these alterations, actin dynamics were quantified at cell-cell junctions using fluorescence recovery after photobleaching (FRAP). LifeAct-GFP was expressed in monolayers of MCF10A cells stably transduced with control or obscurin shRNA-1 (FIG. 4A) in order to visualize actin in live cells. Fluorescence intensity due to LifeAct-GFP expression was very intense at cell-cell borders of MCF10A obscurin-depleted cells, prior to photobleaching (FIG. 4A, pre-bleach panel). However, it was markedly attenuated in the exposed region, following photobleaching (FIG. 4A, bleach panel). Approximately 2.5 min later, the fluorescence intensity recovered at the cell-cell border, though not completely (FIG. 4A; 8.6 sec and 200 sec panel). Analysis of FRAP data (FIG. 4B) revealed that the mobile fraction of LifeAct-GFP molecules was considerably larger in obscurin-KD MCF10A cells relative to control cells (FIG. 4C), whereas no significant difference was noted on the half-life of LifeAct-GFP recovery (FIG. 4D). Collectively, these data indicate that loss of giant obscurins from MCF10A cells results in the formation of membrane protrusions highly enriched in actin filaments, which exhibit increased dynamics compared to control cells.

Example 26

Figure 5A:
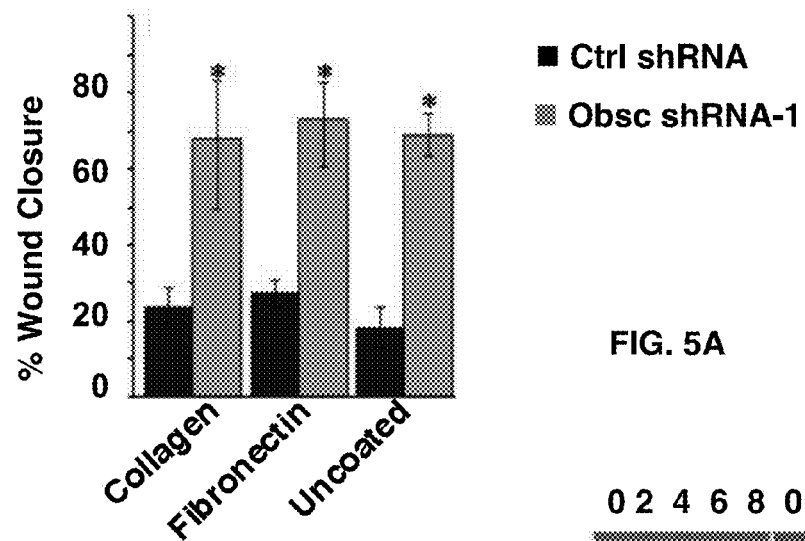
FIGS. 5A-5F show that Obscurin-depleted MCF10A cells exhibit increased motility and invasiveness in vitro.

Depletion of Obscurins from Breast Epithelial Cells Promotes Migration and Invasion Whether the alterations in actin dynamics in obscurin-depleted MCF10A cells were associated with an increase in cell migration and invasion was examined. Fluorescence imaging of LifeAct-GFP indicated that obscurin-KD, but not control, cells displayed increased migration and persistence along 2D substrates. To quantitatively study the migratory potential of obscurin-depleted MCF10A cells, a wound healing assay was used in which stable clones of control or obscurin shRNA-1 cells were plated on collagen, fibronectin, or uncoated wells. MCF10A cells lacking giant obscurins exhibited significantly increased directional migration as a sheet compared to control cells, after a 12-hour incubation period either in the presence of collagen or fibrinectin (FIG. 5A). A marked difference between obscurin-KD and scramble control cells was also detected in the absence of a substrate, indicating that obscurin-depleted cells are capable of migrating in a substrate-independent fashion, presumably due to their inability to form stable adhesion contacts.

Figure 5B:
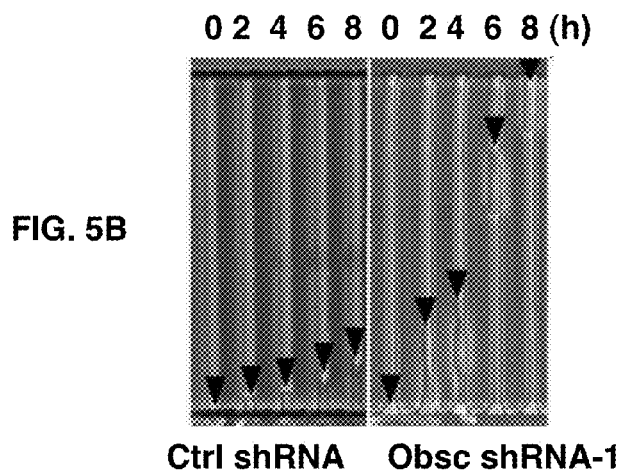
Figure 5C:
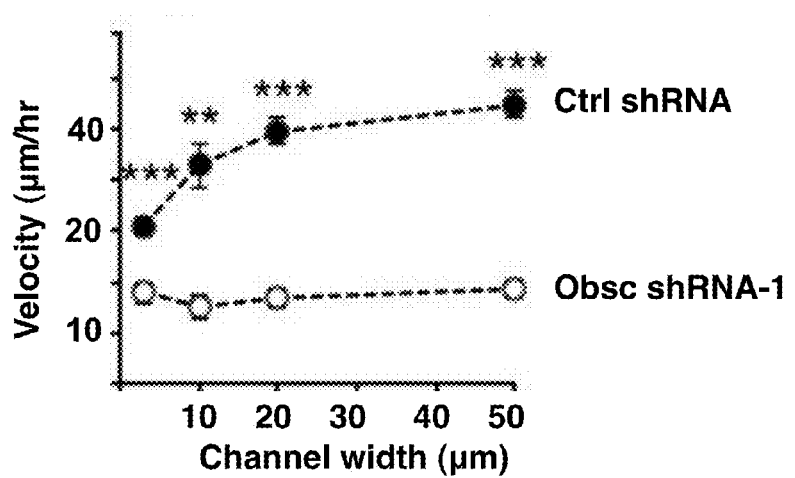
Figure 5D:
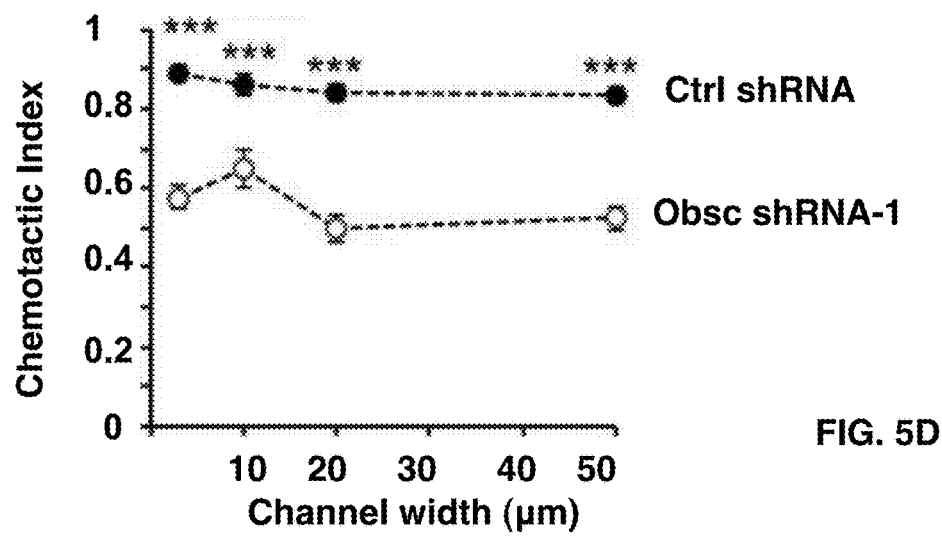

The effects of obscurin-KD on single cell motility through microchannels of varying widths, i.e. 3, 10, 20, and 50 mm) was evaluated using a microfluidic-based migration chamber combined with live cell phase contrast imaging (FIG. 5B) (4, 9, 26, 43). Obscurin-depleted MCF10A cells migrated faster (FIG. 5C) and more persistently (FIG. 5D) than scramble control MCF10A cells, as evidenced by their higher migration velocity and chemotactic index, which represents the ratio of the net cell displacement to the total distance traveled by the cell. MCF10A cells stably transduced with obscurin shRNA-2 showed similarly increased migration in both wound healing and microchannel assays compared to scramble control cells.

Figure 5E:
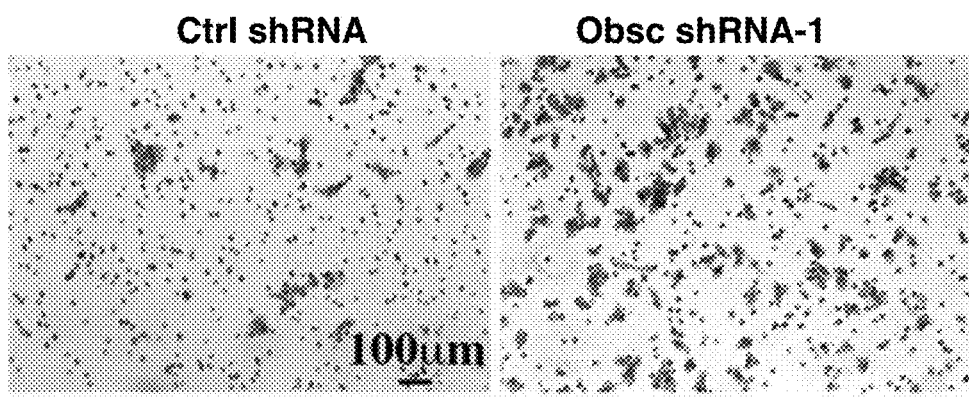
Figure 5F:
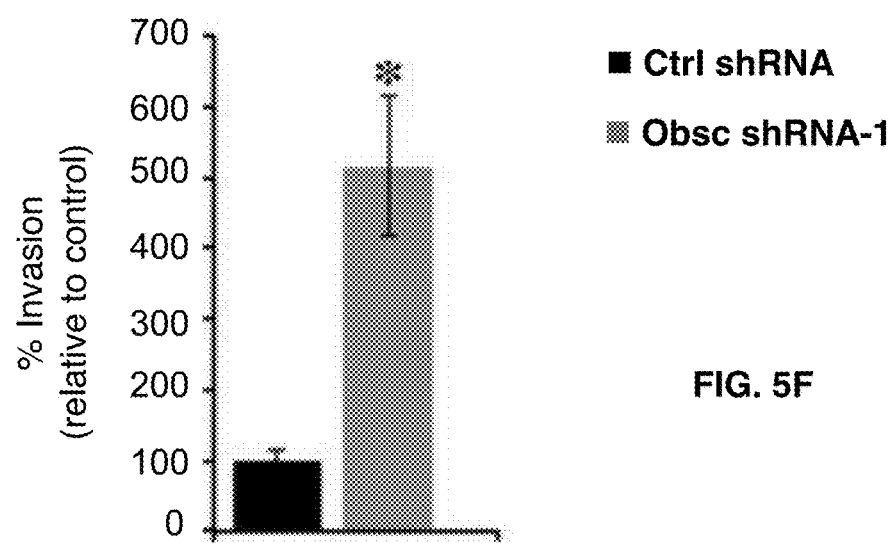

The invasive potential of obscurin-depleted MCF10A cells was examined through a matrigel-coated chamber. Similar to the wound healing and microchannel assays, loss of giant obscurins dramatically increased the invasiveness of MCF10A breast epithelial cells (>400%) compared to scramble control cells (FIGS. 5E-5F). Taken altogether, the present invention demonstrates that depletion of giant obscurins from breast epithelial cells significantly increases their migratory and invasive potentials.

Example 27

Downregulation of Giant Obscurins Promotes Tumorigenicity and Distant Colonization In Vivo Because loss of giant obscurins in MCF10A cells is associated with increased growth and stemness as well as induction of EMT and increased motility and invasiveness in vitro, its effects on tumorigenicity and distant colonization in vivo were examined. Since the MCF10A mammary epithelial cell line is highly resistant to tumor development, multiple genetic alterations are typically needed to promote robust tumor formation (12, 23, 45). For this reason, an MCF10A cell line that stably expresses an activated form of K-Ras was used to provide a weakly tumorigenic background to test the specific contribution of obscurins (or lack thereof) to tumor progression (12, 23, 45). The tumorigenic potential of MCF10A cells stably expressing active K-Ras oncogene and obscurin shRNA-1 (Ras/Obsc shRNA-1) or K-Ras and scramble control shRNA (Ras/ctrl shRNA) was assessed in a subcutaneous model in adult NSG mice.

Tumors were scored following transplantation. Scores for necrosis were determined by histological evaluation, and correspond to 0=no tumor, 1=<5% necrosis, 2=5-25% necrosis, and 3=>25% necrosis. Scores for tumor size were based on digital caliper measurements, and correspond to 0=no tumor, 1=<0.1 $cm^3$, 2=0.1-1 $cm^3$ and 3=>1 $cm^3$. Lastly, scores of tumor grade were calculated from the sum of the necrosis and tumor size scores, and correspond to grade 0=total score 0, grade 1=total score 1-2, grade 2=total score 3-4, and grade 3=total score 5-6. N/A: not available, due to the small size of the tumor.

Figure 6A:
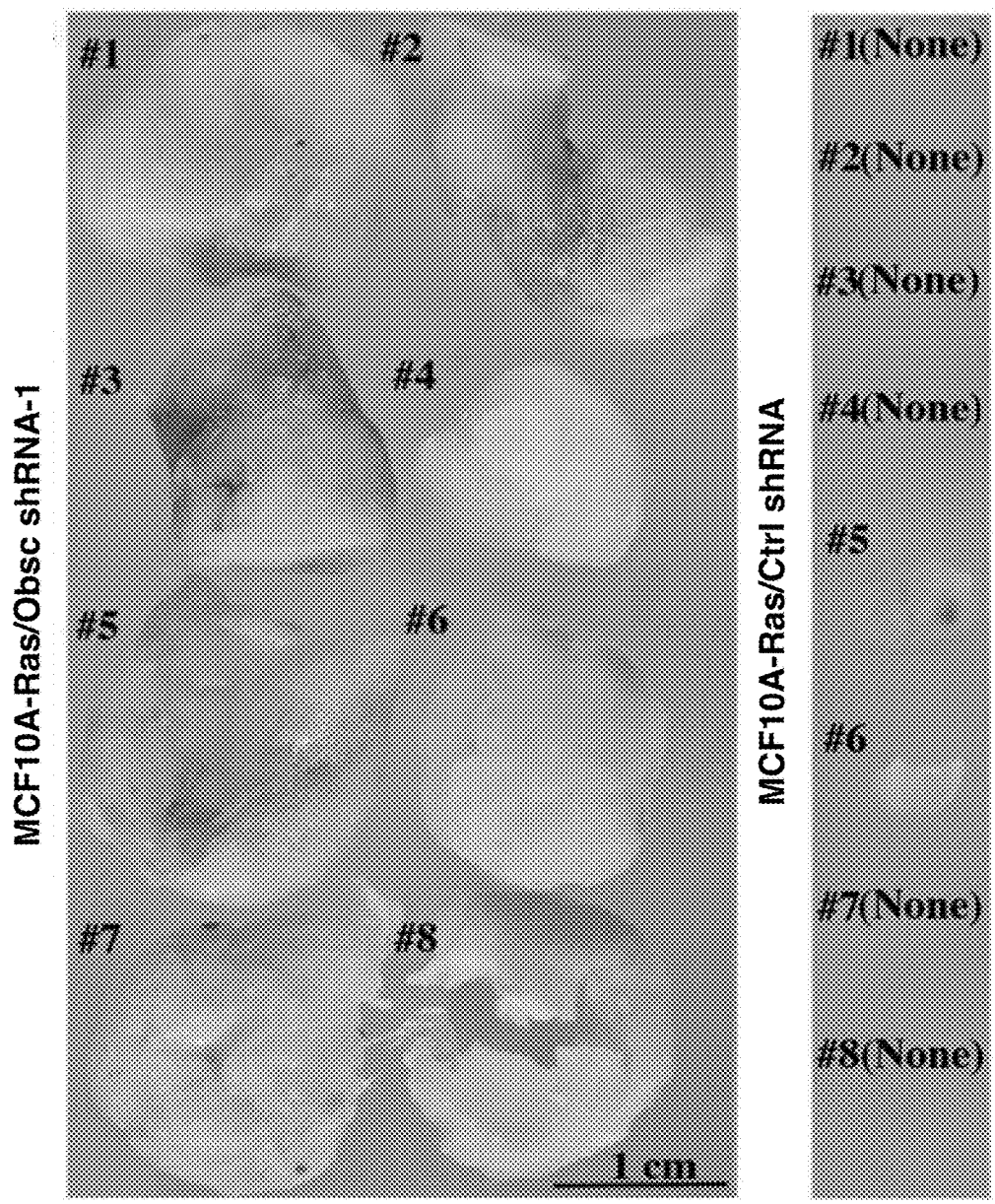
FIGS. 6A-6D show that MCF10A cells stably transduced with obscurin shRNA-1 and the K-Ras oncogene form primary and distant tumors in a subcutaneous and an experimental metastasis model, respectively.

Large (>1 $cm^3$) primary tumors of high grade (grade 3) were detected in all (8/8) mice injected with Ras/Obsc shRNA-1 cells 9 weeks post-injection, as evidenced by gross morphological (FIG. 6A, left) and histological analysis. In contrast, 6 out of 8 mice (6/8) subcutaneously transplanted with Ras/ctrl shRNA cells were devoid of tumors, while 2 out of 8 mice (2/8) developed small (<0.1 $cm^3$) low grade (grade 1) tumors (FIG. 6A, right).

Figure 6B:
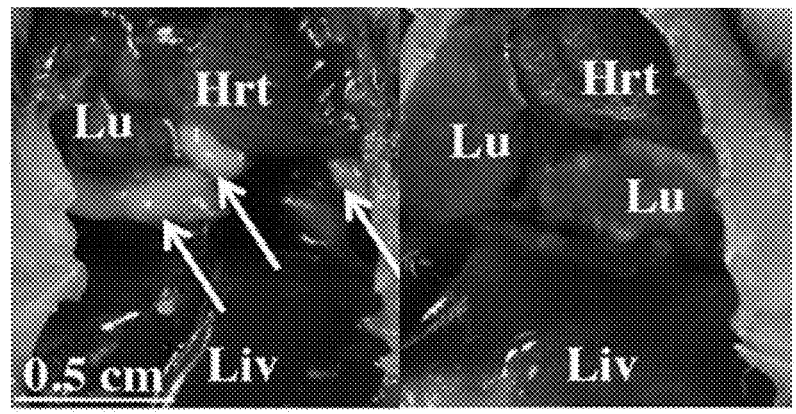
Figure 6C:
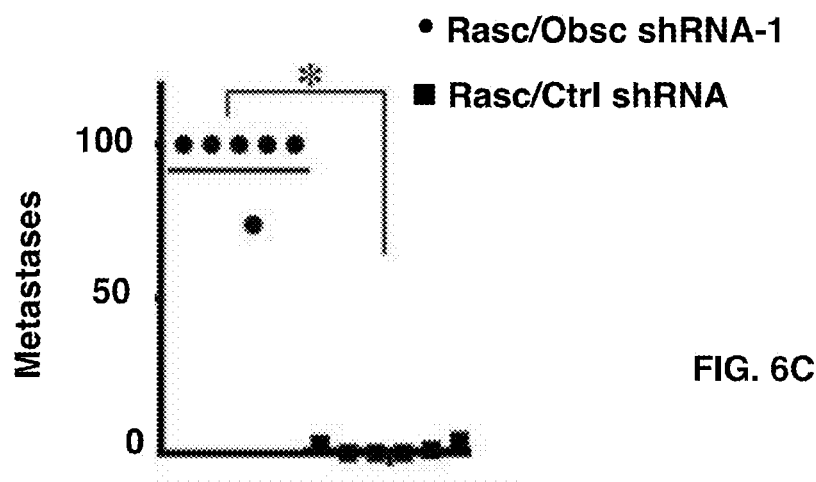
Figure 6D:
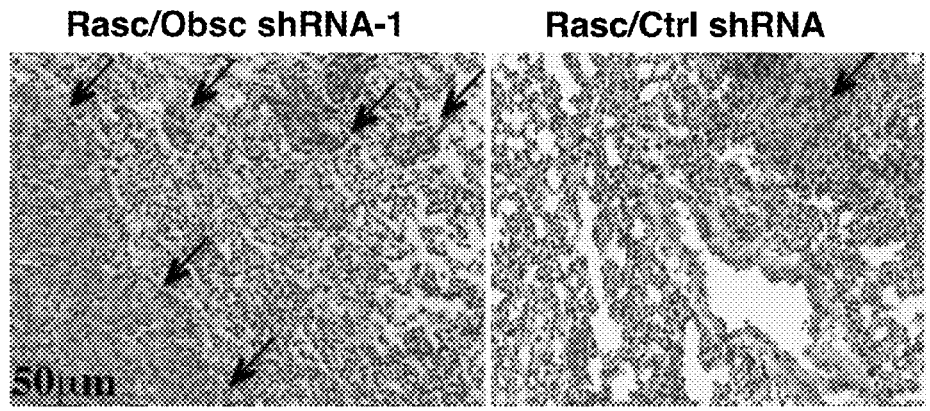

The ability of Ras/Obsc shRNA-1 or Ras/ctrl shRNA MCF10A cells to form lung tumors was examined in a tail vein injection model. Indeed, all (6/6) mice injected with Ras/Obsc shRNA-1 cells via their tail vein exhibited high levels of lung micrometastases (68 to >100 foci per section) by 9 weeks post-injection (FIGS. 6B left, 6C, 6D, left). In contrast, of the 6 mice injected with Ras/ctrl shRNA cells 3 (3/6) had no micrometastases, while 3 (3/6) developed few lung metastatic foci (1-4 foci per section) (FIG. 6B right, 6C, 6D, right). hLINE-1 analysis (13, 15, 37) quantitatively confirmed the presence of human DNA in the lungs of all mice injected with Ras/Obsc shRNA-1 cells. In contrast, only 2 out of 6 mice (2/6) injected with Ras/ctrl shRNA cells displayed appreciable levels of human DNA. Collectively, these findings indicate that loss of giant obscurins in the presence of an active oncogene markedly potentiates the tumorigenic and metastatic potentials of breast epithelial cells.

Table 2 shows the results of the hLINE-1 quantification of the presence of human DNA in the lungs of mice injected with Ras/Obsc shRNA-1 or Ras/Ctrl shRNA cells using qPCR for hLINE-1. Results for Ras/Obsc shRNA-1 are not available for Animal #6 due its death.

TABLE 2

| pg/μL hLINE-1 DNA | |
|---|---|
| Ras/Obsc shRNA-1 | Ras/Ctrl shRNA |
| Animal #1: 935 | Animal #1: 0.05 |
| Animal #2: 241 | Animal #2: 360 |
| Animal #3: 748 | Animal #3: 22.9 |
| Animal #4: 572 | Animal #4: 0.38 |
| Animal #5: 180 | Animal #5: 0.34 |
| Animal #6: N/A | Animal #6: 0.07 |

Figure 7:
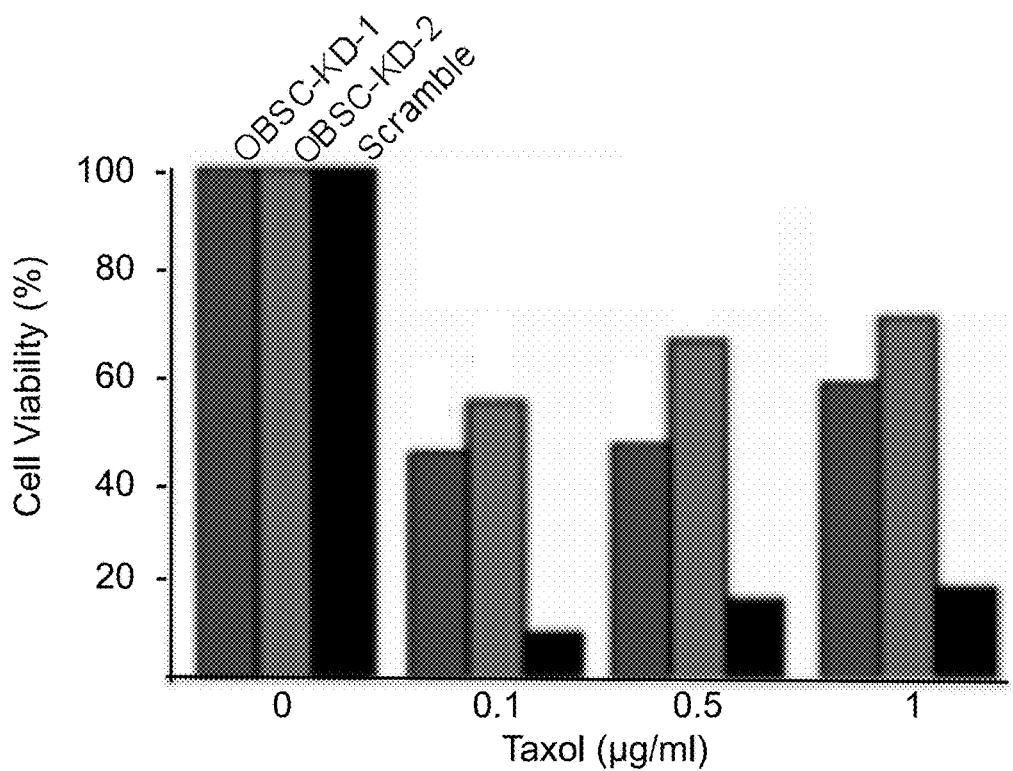
FIG. 7 shows the effects of paclitaxel (taxol) on cell viability of obscurin-KD MCF10A cells compared to controls; statistical significance was examined with Student's t-test (p<0.05), and is denoted with an (*).

The present invention demonstrates that the expression levels of giant obscurins are dramatically reduced in advanced stage breast cancer biopsies. Moreover, loss of giant obscurins results in major cytoskeletal alterations leading to increased cell growth, motility and invasion. Non-tumorigenic MCF10A cells depleted of giant obscurins show reduced sensitivity to chemotherapeutic drugs, such as etoposide and paclitaxel (FIG. 7). FIG. 7 shows the effects of paclitaxel (taxol) on cell viability of obscurin-KD MCF10A cells compared to controls. Thus, breast cancer cells may have different responses to cytoskeletal-targeting chemotherapies depending on the relative expression of giant obscurins.

Example 28

Generation of the Obscurin SH3-RhoGEF-PH Cassette in Lentivirus Vector

A mini-obscurin (~40 kDa) containing the tripartite signaling cassette was developed which consists of tandem src homology 3 (SH3) domain, Rho Guanine Nucleotide Exchange Factor (RhoGEF) motif and Pleckstrin Homology (PH) domain, referred to as the SH3-RhoGEF-PH cassette. Using standard molecular cloning techniques, the cDNA encoding the obscurin SH3-RhoGEF-PH cassette was introduced into a DNA vector that was in turn incorporated into a lentiviral vector. Lentiviruses allow permanent insertion of exogenous DNA (such as the SH3-RhoGEF-PH cassette) into a cell's genomic DNA using the cell's own machinery. This ensures that the introduced fragment of obscurin, i.e. the SH3-RhoGEF-PH cassette, is continuously produced, and thus capable of suppressing the migratory and invasive potentials of cancer cells.

Example 29

Effects of SH3-RhoGEF-PH Cassette

Figure 8A:
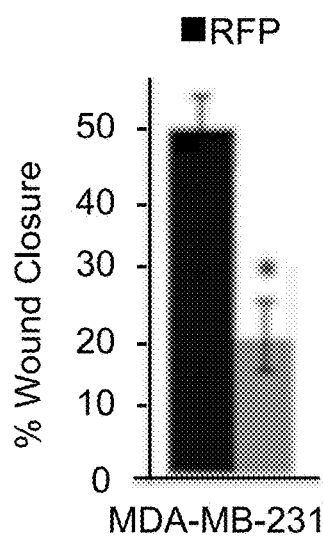
FIGS. 8A-8B show that metastatic MDAMB-231 cells show reduced motility and invasion.
Figure 8B:
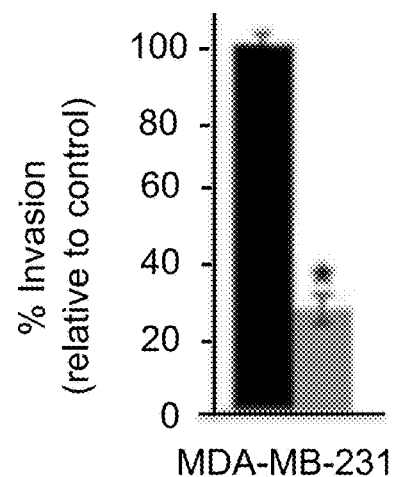

The present invention demonstrates that overexpression of the fragment of giant obscurins composed of tandem src homology 3-Rho guanine exchange factor-pleckstrin homology (obscurin SH3-RhoGEF-PH) signaling cassette suppresses tumorigenesis and metastasis in vivo. Ectopic expression of the obscurin SH3-RhoGEF-PH cassette in different metastatic breast cancer cell lines (e.g. MDA-MB-231 and Bt-549) via lentiviral infection suppresses cell migration and invasion by ~30% and ~70%, respectively (FIG. 8, n=3, t-test, $p<0.05$). Thus, overexpression of the SH3-RhoGEF-PH cassette induces mesenchymal to epithelial transition (MET), alters cytoskeletal re-organization, suppresses PI3K/Akt and/or MAPK transactivation and Matrix Metallo-Proteinase (MMP) synthesis.

Example 30

Effect of the SH3-RhoGEF-PH Cassette on In Vivo Tumorigenesis and Metastasis

To demonstrate the metastasis suppressing role of the obscurin signaling cassette in vivo, the two selected breast cancer tumorgrafts that exhibit the lowest expression of giant obscurins and stably overexpress the SH3-RhoGEF-PH cassette and the luciferase gene are injected orthotopically (i.e. into the mammary fat pad) or systemically (i.e. via the tail vein) in NOD-SCID IL2Rγ null mice. In control experiments, syngeneic NOD-SCID IL2Rγ null mice of the same age are inoculated with breast cancer cells transduced with "empty" lentivirus and luciferase vectors. Solid tumor burden and circulating tumor cells are monitored over time using bioluminescence imaging and qPCR for the hLINE gene. Ectopic expression of the SH3-RhoGEF-PH cassette in metastatic breast cancer cells induces MET, represses the rate of actin filament assembly and disassembly, suppresses Focal Adhesion (FA) turnover, and alter microtubule (MT) dynamics rendering cells less migratory and less metastatic. SH3-RhoGEF-PH overexpression is effective in markedly suppressing the invasion of all metastatic breast cancer cells, since it regulates the transactivation of the PI3K and MAPK pathways, which are in turn responsible for the synthesis of different MMPs. Moreover, animals injected with breast cancer cells expressing the SH3-RhoGEF-PH cassette are expected to exhibit significantly reduced numbers of primary tumors and rates of micro- and macro-metastases.

The ability of obscurin knockdown cells to metastasize via the formation of microtentacles and the ability of the RhoGEF motif to dimish their formation following restoration of its expression was examined. Phosphorylation of RhoA effectors, including myosin phosphatase, myosin light chain, Lim kinase, and cofilin, was reduced upon obscurin knockdown in both attached and suspended cells, resulting in decreased actomyosin contractility and increased dynamic actin, and allowing the suspended cells to escape detachment-induced apoptosis. These conditions, along with the concomitant upregulation of the microtubule-stabilizing factors, detyrosinated α-tubulin and vimentin, cause shObsc-expressing cells to extend microtentacles, microtubule-based projections that mediate attachment of circulating tumor cells to the endothelium. MCF10A cells expressing shObsc more readily attach and spread than shCtrl cells do. The attachment advantage held by shObsc cells persists following paclitaxel treatment, and is accompanied by increased viability after taxane exposure. Extension of microtentacles is significantly reduced, returning to control levels, following overexpression of the obscurin RhoGEF motif. Thus, the present invention demonstrates that loss of obscurins represents a substantial selective advantage for breast epithelial cells during metastasis, with the obscurin-deficient cells better able to attach even following taxane treatment. Absence of obscurins is a significant risk factor for the development of metastasis, and that treatment with paclitaxel may exacerbate this advantage by selectively allowing only stem-like obscurin-deficient cells to attach to the endothelium of distant sites, a first step towards colonizing metastatic tumors. Restoration of the expression of the obscurin RhoGEF motif diminishes the ability of these cells to form extensions that allow their re-attachment and spreading (i.e. to seed new metastatic colonies).

DISCUSSION

Cancer is a disease caused by alterations in multiple genes, which promote cell growth, decrease apoptosis, and increase cell motility and invasion (22). Down-regulation of giant obscurins in breast epithelial cells results in increased cell survival following exposure to DNA stress due to decreased apoptosis (33). The present invention demonstrates that loss of giant obscurins also provides mammary epithelial cells with a growth advantage as seen by the ability of obscurin-KD cells to robustly form both primary and secondary mammospheres. Notably, ~40% of the primary mammosphere population bears the CD44$^+$/CD24$^-$ signature, which is indicative of cell stemness, thereby suggesting that loss of giant obscurins leads to enrichment of a cell population with tumor-initiating potential. Consistent with these observations, giant obscurins exhibit markedly reduced expression in advanced stage (grade 2 or higher) human breast cancer biopsies of ductal and lobular differentiation, suggesting that their loss may correlate with undifferentiated, more aggressive and metastasis-prone tumors. Interestingly, when residual obscurins, representing truncated and/or mutant forms, were detected they exhibited a cytoplasmic punctate distribution, potentially corresponding to lysosomal accumulations.

A critical step in cancer progression is the disruption of AJs, resulting in decreased cell-cell adhesion, which promotes motility and contributes to the invasion and metastasis of cancer cells (7, 18, 27). Obscurin-KD cells displayed increased cell scattering commensurate with a more mesenchymal appearance compared to control cells, which formed epithelial sheets (33). This phenotypic alteration is accompanied by reduced expression and disrupted localization of major epithelial junctional proteins like N-cadherin, b-catenin, connexin-43, plakoglobin and claudin-1. Disruption of the E-cadherin/β-catenin complex increases the pool of cytoplasmic and nuclear β-catenin, which can induce the initiation of aberrant Wnt signaling (20, 44). Nuclear β-catenin, in conjunction with T-Cell Factor (TCF) and Lymphocyte Enhancer Transcription Factor (LEF), promotes the transcription of multiple genes, which in turn can lead to abnormal cell cycle progression and uncontrollable growth (24). Knockdown of giant obscurins in MCF10A cells resulted in near loss of β-catenin from cell-cell junctions that was accompanied by accumulation of residual protein in the nucleus, suggesting that loss of giant obscurins may result in increased cell survival and growth due to deregulated β-catenin mediated transcription. It is noteworthy that most of the changes observed in the expression levels of junctional proteins do not correspond to similar changes in their transcript levels, indicating that giant obscurins may play key roles in maintaining and stabilizing proteins in cell-cell junctions. This is reminiscent of the scaffolding role of giant obscurins in striated muscle cells, where they provide binding sites to diverse cytoskeletal and membrane-associated proteins via their tandem adhesion and signaling motifs (28, 30, 31).

The disruption of AJs occurring at the onset of cancer metastasis is followed by EMT, a process through which epithelial cells dedifferentiate, and acquire a mesenchymal phenotype that increases their motility and invasiveness (17, 40). Depletion of giant obscurins from MCF10A cells results in a significant increase of the amounts of major mensenchymal proteins, such as N-cadherin and vimentin, and of the transcriptional regulators Slug and Twist. Interestingly, Slug and Twist are known transcriptional repressors of E-cadherin expression (14, 42), suggesting that their upregulation may be contributing to changes seen in the E-cadherin levels. These findings thus reveal that giant obscurins are critical to maintaining the junctional organization, polarity and stability of breast epithelial cells, therefore precluding their de-differentiation followed by the accumulation of mesenchymal proteins.

The acquisition of EMT is accompanied by increased cell motility and invasion (17), and is thought to enable tumor cells to migrate from the primary tumor to distant secondary sites (11). Obscurin-depleted MCF10A cells exhibit increased and persistent migration, as evidenced by wound healing and single cell migration assays. Metastasizing tumor cells are also capable of degrading and invading through the surrounding basement membrane of distant organs and tissues (8). Indeed, down-regulation of giant obscurins promotes cell invasion through a matrigel chamber. It therefore appears that loss of giant obscurins from breast epithelium may contribute to multiple steps during tumor formation and metastasis.

Enhanced cell migration is accompanied by increased formation of actin rich protrusions, such as filopodia, at the leading edge of the cell, which are required for cell propulsion (2). The formation of these protrusions is used by cells to extend forward into their surroundings, and is accompanied by increased actin dynamics (10). Loss of giant obscurins in mammary epithelial cells resulted in the formation of numerous filopodia-like protrusions near the regions of cell-cell contact. FRAP analysis revealed increased actin dynamics in obscurin-KD cells relative to controls. Thus, the increased migratory potential of obscurin-depleted cells appears to be due to altered cell-cell junctions and increased actin dynamics. The Rho family of GTPases and their regulators are involved in cell motility (21). Giant obscurins contain a RhoGEF motif, which specifically activates RhoA, a major regulator of actin microfilaments (16). It is therefore plausible that loss of giant obscurins leads to deregulated RhoA signaling, which has been intimately associated with the development and progression of metastatic breast cancer.

Loss of giant obscurins in the presence of active K-Ras imparts tumorigenic, migratory and invasive capabilities to breast epithelial cells, as demonstrated by the rapid formation of large primary tumors in a subcutaneous model and lung trapping in an experimental metastasis model. Importantly, Ras is insufficient to transform MCF10A cells to a fully tumorigenic and metastatic phenotype in mice (45). However, co-expression of Ras and Bmi-1, a stemness-inducing factor, promotes MCF10A tumorgenicity and metastasis in vivo (23). Similarly, these findings demonstrate that concomitant loss of giant obscurins and expression of active Ras result in the rapid formation of primary and distant tumors, which exhibit morphological (size>1 cm$^3$) and histological (grade 3) characteristics indicative of less differentiated and thus more aggressive tumors.

In summary, the present invention demonstrates that loss of giant obscurins from breast epithelial cells results in major cytoskeletal and signaling alterations, which are essential for both local tumor formation and distant colonization, suggesting that giant obscurins may play tumor and metastasis suppressive roles.

The following references are cited herein:
1. Ackermann et al., Molecular Biology of the Cell 2009; 20: 2963-2978.
2. Arjonen et al., Cell Adh Migr 2011; 5: 421-430.
3. Balakrishnan et al., Cancer Research 2007; 67: 3545-3550.
4. Balzer et al., FASEB J 2012; 26: 4045-4056.
5. Baum et al., The Journal of Cell Biology 2011; 192: 907-917.

6. Borisov et al., Journal of Cellular Biochemistry 2008; 103: 1621-1635.
7. Brasch et al., Trends Cell Biol 2012; 22: 299-310.
8. Bravo-Cordero et al., Curr Opin Cell Biol 2012; 24: 277-283.
9. Chen et al., Sci Rep 2013; 3: 1870.
10. Chhabra et al., Nat Cell Biol 2007; 9: 1110-1121.
11. Chiang et al., N Engl J Med 2008; 359: 2814-2823.
12. Ciardiello et al., Molecular carcinogenesis 1992; 6: 43-52.
13. Dallas et al., FASEB J 2012; 26: 2648-2656.
14. Drasin et al., Breast Cancer Res 2011; 13: 226.
15. Ericson et al., PNAS 2010; 107: 2598-2603.
16. Ford-Speelman et al., Molecular Biology of the Cell 2009; 20: 3905-3917.
17. Foroni et al., Cancer Treat Rev 2012; 38: 689-697.
18. Friedl et al., Cell 2011; 147: 992-1009.
19. Fukuzawa et al., Journal of Muscle Research and Cell Motility 2005; 26: 427-434.
20. Gottardi et al., J Cell Biol 2001; 153: 1049-1060.
21. Hall A. Rho family GTPases. Biochem Soc Trans 2012; 40: 1378-1382.
22. Hanahan et al., Cell 2011; 144: 646-674.
23. Hoenerhoff et al., Oncogene 2009; 28: 3022-3032.
24. Holland et al., Current Opinion in Cell Biology 2013; 25: 254-264.
25. Hu et al., FASEB J 2013; 27: 2001-2012.
26. Hung et al., J Cell Biol 2013; 202: 807-824.
27. Knights et al., Trends in Cancer Research 2012; 8: 61-69.
28. Kontrogianni-Konstantopoulos et al., Molecular Biology of the Cell 2003; 14: 1138-1148.
29. Kontrogianni-Konstantopoulos et al., Journal of Muscle Research and Cell Motility 2005; 26: 419-426.
30. Kontrogianni-Konstantopoulos et al., FASEB J 2006; 20: 2102-2111.
31. Kontrogianni-Konstantopoulos et al., Physiol Rev 2009; 89: 1217-1267.
32. Nanda et al., PNAS 2006; 103: 3351-3356.
33. Perry et al., FASEB J 2012; 26: 2764-2775.
34. Perry et al., IUBMB life 2013; 65: 479-486.
35. Phillips et al., J Natl Cancer Inst 2006; 98: 1777-1785.
36. Price et al., PNAS 2007; 104: 3414-3419.
37. Rago et al., Cancer Research 2007; 67: 9364-9370.
38. Russell et al., Gene 2002; 282: 237-246.
39. Samuels et al., Cancer Cell 2005; 7: 561-573.
40. Scheel et al., Seminars in Cancer Biology 2012; 22: 396-403.
41. Sjoblom et al., Science 2006; 314: 268-274.
42. Taube et al., PNAS USA 2010; 107: 15449-15454.
43. Tong et al., PLoS One 2012; 7: e29211.
44. Valenta et al., The EMBO Journal 2012; 31: 2714-2736.
45. Wang et al., Anticancer Research 1997; 17: 4387-4394.

What is claimed is:

1. A method of evaluating potential for invasiveness, metastasis, or recurrence of a breast cancer of grade 2 or grade 3, comprising the steps of: obtaining a breast tissue sample of tumor cells or suspected tumor cells from a subject; contacting said sample with an antibody generated against a fusion protein comprising obscurin Ig domains 58/59 with the sequence shown in SEQ ID NO: 27; detecting expression levels or subcellular distribution of giant obscurin proteins in said sample; and assessing the expression levels or the subcellular distribution of the giant obscurin proteins in said cells, wherein a decreased expression level or altered distribution of the giant obscurin proteins in the cells of the sample, in comparison to a control non-invasive standard or to a sample taken from the subject at a different point in time, is indicative of an increased potential of at least one of the invasiveness, metastasis, or recurrence of the breast cancer.

2. The method of claim 1, wherein the step of detecting the expression levels or the subcellular distribution of giant obscurin proteins is performed by at least one selected from the group, immunoblotting an electrophotogram, immunohistochemistry, or immunofluorescence.

3. The method of claim 2, wherein said giant obscurin protein has a size of about 720 kDa.

4. The method of claim 2, wherein said giant obscurin protein has a size of about 870 kDa.

* * * * *

SEQUENCE LISTING

```
<160> NUMBER OF SEQ ID NOS: 27

<210> SEQ ID NO 1
<211> LENGTH: 18
<212> TYPE: DNA
<213> ORGANISM: Artificial sequence
<220> FEATURE:
<223> OTHER INFORMATION: E-cadherin forward primer

<400> SEQUENCE: 1
atcaggcctc cgtttctg                                                 18

<210> SEQ ID NO 2
<211> LENGTH: 18
<212> TYPE: DNA
<213> ORGANISM: Artificial sequence
<220> FEATURE:
<223> OTHER INFORMATION: E-cadherin reverse primer

<400> SEQUENCE: 2
gcagctgatg ggaggaat                                                 18

<210> SEQ ID NO 3
<211> LENGTH: 21
<212> TYPE: DNA
<213> ORGANISM: Artificial sequence
<220> FEATURE:
<223> OTHER INFORMATION: Beta-catenin forward primer

<400> SEQUENCE: 3
gaaaatccag cgtggacaat g                                             21

<210> SEQ ID NO 4
<211> LENGTH: 18
<212> TYPE: DNA
<213> ORGANISM: Artificial sequence
<220> FEATURE:
<223> OTHER INFORMATION: Beta-catenin reverse primer
```

```
<400> SEQUENCE: 4
acgcatgata gcgtgtct                                                   18

<210> SEQ ID NO 5
<211> LENGTH: 17
<212> TYPE: DNA
<213> ORGANISM: Artificial sequence
<220> FEATURE:
<223> OTHER INFORMATION: Alpha-catenin forward primer

<400> SEQUENCE: 5
gtggggctgc cttgatg                                                    17

<210> SEQ ID NO 6
<211> LENGTH: 18
<212> TYPE: DNA
<213> ORGANISM: Artificial sequence
<220> FEATURE:
<223> OTHER INFORMATION: Alpha-catenin reverse primer

<400> SEQUENCE: 6
aattgcacca gctgtgcg                                                   18

<210> SEQ ID NO 7
<211> LENGTH: 16
<212> TYPE: DNA
<213> ORGANISM: Artificial sequence
<220> FEATURE:
<223> OTHER INFORMATION: p120 catenin forward primer

<400> SEQUENCE: 7
cagctgctat gcgggt                                                     16

<210> SEQ ID NO 8
<211> LENGTH: 19
<212> TYPE: DNA
<213> ORGANISM: Artificial sequence
<220> FEATURE:
<223> OTHER INFORMATION: p120 catenin reverse primer

<400> SEQUENCE: 8
acctccttct ggttgctct                                                  19

<210> SEQ ID NO 9
<211> LENGTH: 20
<212> TYPE: DNA
<213> ORGANISM: Artificial sequence
<220> FEATURE:
<223> OTHER INFORMATION: N-cadherin forward primer

<400> SEQUENCE: 9
cctgcttcag gcgtctgtag                                                 20

<210> SEQ ID NO 10
<211> LENGTH: 20
<212> TYPE: DNA
<213> ORGANISM: Artificial sequence
<220> FEATURE:
<223> OTHER INFORMATION: N-cadherin reverse primer

<400> SEQUENCE: 10
ctgcctttgt aggtggccac                                                 20

<210> SEQ ID NO 11
<211> LENGTH: 22
```

```
<212> TYPE: DNA
<213> ORGANISM: Artificial sequence
<220> FEATURE:
<223> OTHER INFORMATION: Vimentin forward primer

<400> SEQUENCE: 11
ggcagaagaa tggtacaaat cc                                          22

<210> SEQ ID NO 12
<211> LENGTH: 20
<212> TYPE: DNA
<213> ORGANISM: Artificial sequence
<220> FEATURE:
<223> OTHER INFORMATION: Vimentin reverse primer

<400> SEQUENCE: 12
cttccagcag cttcctgtag                                             20

<210> SEQ ID NO 13
<211> LENGTH: 16
<212> TYPE: DNA
<213> ORGANISM: Artificial sequence
<220> FEATURE:
<223> OTHER INFORMATION: Slug forward primer

<400> SEQUENCE: 13
ctccattcca cgccca                                                 16

<210> SEQ ID NO 14
<211> LENGTH: 19
<212> TYPE: DNA
<213> ORGANISM: Artificial sequence
<220> FEATURE:
<223> OTHER INFORMATION: Slug reverse primer

<400> SEQUENCE: 14
aatgggtctg cagatgagc                                              19

<210> SEQ ID NO 15
<211> LENGTH: 20
<212> TYPE: DNA
<213> ORGANISM: Artificial sequence
<220> FEATURE:
<223> OTHER INFORMATION: Twist forward primer

<400> SEQUENCE: 15
gagtccgcag tcttacgagg                                             20

<210> SEQ ID NO 16
<211> LENGTH: 20
<212> TYPE: DNA
<213> ORGANISM: Artificial sequence
<220> FEATURE:
<223> OTHER INFORMATION: Twist reverse primer

<400> SEQUENCE: 16
ctgcccgtct gggaatcact                                             20

<210> SEQ ID NO 17
<211> LENGTH: 20
<212> TYPE: DNA
<213> ORGANISM: Artificial sequence
<220> FEATURE:
<223> OTHER INFORMATION: Claudin-1 forward primer

<400> SEQUENCE: 17
```

-continued gcagcacatt gcaagcaacc					20

<210> SEQ ID NO 18
<211> LENGTH: 17
<212> TYPE: DNA
<213> ORGANISM: Artificial sequence
<220> FEATURE:
<223> OTHER INFORMATION: Claudin-1 reverse primer

<400> SEQUENCE: 18
cgctggaagg tgcaggt					17

<210> SEQ ID NO 19
<211> LENGTH: 19
<212> TYPE: DNA
<213> ORGANISM: Artificial sequence
<220> FEATURE:
<223> OTHER INFORMATION: ZO-1 forward primer

<400> SEQUENCE: 19
caccaagtac tgaggcagc					19

<210> SEQ ID NO 20
<211> LENGTH: 18
<212> TYPE: DNA
<213> ORGANISM: Artificial sequence
<220> FEATURE:
<223> OTHER INFORMATION: ZO-1 reverse primer

<400> SEQUENCE: 20
tggactctgc aggcttgg					18

<210> SEQ ID NO 21
<211> LENGTH: 19
<212> TYPE: DNA
<213> ORGANISM: Artificial sequence
<220> FEATURE:
<223> OTHER INFORMATION: Plakoglobin forward primer

<400> SEQUENCE: 21
cagtagccac gatggaggt					19

<210> SEQ ID NO 22
<211> LENGTH: 17
<212> TYPE: DNA
<213> ORGANISM: Artificial sequence
<220> FEATURE:
<223> OTHER INFORMATION: Plakoglobin reverse primer

<400> SEQUENCE: 22
cgacgcctcc ttcttcg					17

<210> SEQ ID NO 23
<211> LENGTH: 20
<212> TYPE: DNA
<213> ORGANISM: Artificial sequence
<220> FEATURE:
<223> OTHER INFORMATION: Connexin-43 forward primer

<400> SEQUENCE: 23
agcgccttag gcaaactcct					20

<210> SEQ ID NO 24
<211> LENGTH: 20
<212> TYPE: DNA
<213> ORGANISM: Artificial sequence

```
<220> FEATURE:
<223> OTHER INFORMATION: Connexin-43 reverse primer

<400> SEQUENCE: 24
atcagcaaga aggccacctc                                              20

<210> SEQ ID NO 25
<211> LENGTH: 22
<212> TYPE: DNA
<213> ORGANISM: Artificial sequence
<220> FEATURE:
<223> OTHER INFORMATION: mouse DNA forward primer

<400> SEQUENCE: 25
tcactcaaag ccgctcaact ac                                           22

<210> SEQ ID NO 26
<211> LENGTH: 24
<212> TYPE: DNA
<213> ORGANISM: Artificial sequence
<220> FEATURE:
<223> OTHER INFORMATION: mouse DNA reverse primer

<400> SEQUENCE: 26
tctgccttca tttcgttatg tacc                                         24

<210> SEQ ID NO 27
<211> LENGTH: 182
<212> TYPE: PRT
<213> ORGANISM: Artificial sequence
<220> FEATURE:
<223> OTHER INFORMATION: sequence of K528-1-L5462 antigen

<400> SEQUENCE: 27
```

Lys Asn Thr Val Leu Arg Gly Leu Glu Asn Val Asp Ala Leu Glu Gly
 1               5                  10                  15

Gly Glu Ala Leu Phe Glu Cys Gln Leu Ser Gln Pro Glu Val Ala Ala
            20                  25                  30

His Thr Trp Leu Leu Asp Asp Glu Pro Val His Thr Ser Glu Lys Val
        35                  40                  45

Glu Val Val Tyr Phe Glu Asn Gly Leu Arg His Leu Leu Leu Leu Lys
    50                  55                  60

Asn Leu Lys Pro Gln Asp Ser Cys Arg Val Thr Phe Leu Ala Gly Asp
65                  70                  75                  80

Val Val Thr Ser Ala Phe Leu Thr Val Arg Gly Trp Arg Leu Glu Val
                85                  90                  95

Leu Glu Pro Pro His Asp Ala Ser Val Lys Ala Gly Met Gln Val Arg
            100                 105                 110

Phe Thr Cys Ile Leu Ser Glu Ala Val Pro Val Gly Glu Ala Thr Trp
        115                 120                 125

Tyr Ile Asn Gly Ala Ala Ile Gln Pro Asp Asp Thr Asp Trp Thr Val
    130                 135                 140

Thr Thr Asp Gly Ser His His Ala Leu Thr Leu Ser Asn Ala Gln Pro
145                 150                 155                 160

Gln His Ala Gly Glu Val Thr Phe Ala Ala Arg Asp Ala Val Ala Ser
                165                 170                 175

Ala Arg Leu Ser Val Leu
            180